United States Patent
Mazanec et al.

(10) Patent No.: US 10,646,709 B2
(45) Date of Patent: May 12, 2020

(54) FULLY IMPLANTABLE MODULAR COCHLEAR IMPLANT SYSTEM

(71) Applicant: Envoy Medical Corporation, White Bear Lake, MN (US)

(72) Inventors: Paul R. Mazanec, Ham Lake, MN (US); Benjamin R. Whittington, Maplewood, MN (US); Timothy J. Earnest, Vadnais Heights, MN (US)

(73) Assignee: Envoy Medical Corporation, White Bear Lake, MN (US)

( * ) Notice: Subject to any disclaimer, the term of this patent is extended or adjusted under 35 U.S.C. 154(b) by 235 days.

(21) Appl. No.: 15/679,755

(22) Filed: Aug. 17, 2017

(65) Prior Publication Data

US 2018/0050198 A1 Feb. 22, 2018

Related U.S. Application Data

(60) Provisional application No. 62/376,195, filed on Aug. 17, 2016, provisional application No. 62/376,198, filed on Aug. 17, 2016.

(51) Int. Cl.
*A61N 1/05* (2006.01)
*A61N 1/36* (2006.01)
(Continued)

(52) U.S. Cl.
CPC ........... *A61N 1/0541* (2013.01); *A61N 1/025* (2013.01); *A61N 1/36017* (2013.01);
(Continued)

(58) Field of Classification Search
CPC .. A61N 1/0541; A61N 1/36038; A61N 1/025; A61N 1/36017; A61N 1/36125;
(Continued)

(56) References Cited

U.S. PATENT DOCUMENTS

| 4,400,590 A | 8/1983 | Michelson |
| 4,495,384 A | 1/1985 | Scott et al. |

(Continued)

OTHER PUBLICATIONS

Mazanec et al., unpublished U.S. Appl. No. 15/679,740, entitled Communication System and Methods For Fully Implantable Modular Cochlear Implant System, filed Aug. 17, 2017, 75 pages.
(Continued)

*Primary Examiner* — Lindsey G Wehrheim
(74) *Attorney, Agent, or Firm* — Fredrikson & Byron, P.A.

(57) ABSTRACT

Cochlear implant systems can include a cochlear electrode, a stimulator in electrical communication with the cochlear electrode, and a signal processor in communication with the stimulator. The signal processor can receive an input signal from an input source and output a stimulation signal to the stimulator based on the received input signal and a transfer function of the signal processor. The signal processor can be connected to the stimulator via a first detachable connector configured to detachably connect and provide communication between the signal processor and the stimulator. The signal processor can be connected to the input source via a second detachable connector configured to detachably connect and provide communication between the signal processor and the input source. A modular signal processor can be detached from the stimulator and the input source for repair or replacement.

22 Claims, 19 Drawing Sheets

(51) Int. Cl.
*A61N 1/372* (2006.01)
*A61N 1/378* (2006.01)
*A61N 1/02* (2006.01)
*H04R 25/00* (2006.01)
*A61N 1/08* (2006.01)

(52) U.S. Cl.
CPC ...... *A61N 1/36038* (2017.08); *A61N 1/36125* (2013.01); *A61N 1/36128* (2013.01); *A61N 1/36146* (2013.01); *A61N 1/36192* (2013.01); *A61N 1/372* (2013.01); *A61N 1/3787* (2013.01); *A61N 1/37223* (2013.01); *H04R 25/554* (2013.01); *A61N 1/36039* (2017.08); *A61N 2001/083* (2013.01); *H04R 2225/55* (2013.01); *H04R 2225/61* (2013.01); *H04R 2225/67* (2013.01); *H04R 2430/01* (2013.01)

(58) Field of Classification Search
CPC ............ A61N 1/36128; A61N 1/36146; A61N 1/36192; A61N 1/372; A61N 1/37223; A61N 1/3787; A61N 1/36039; A61N 2001/083; H04R 25/554; H04R 2225/55; H04R 2225/61; H04R 2225/67; H04R 2430/01

See application file for complete search history.

(56) References Cited

U.S. PATENT DOCUMENTS

| | | |
|---|---|---|
| 4,729,366 A | 3/1988 | Schaefer |
| 4,850,962 A | 7/1989 | Schaefer |
| 4,918,745 A | 4/1990 | Hutchison |
| 5,540,095 A | 7/1996 | Sherman et al. |
| 5,762,583 A | 6/1998 | Adams et al. |
| 6,212,431 B1 | 4/2001 | Hahn et al. |
| 6,272,382 B1 * | 8/2001 | Faltys ............... A61N 1/08 607/57 |
| 6,308,101 B1 | 10/2001 | Faltys et al. |
| 6,358,281 B1 | 3/2002 | Berrang et al. |
| 7,319,906 B2 | 1/2008 | Kuzma et al. |
| 7,524,278 B2 | 4/2009 | Madsen et al. |
| 8,554,329 B1 | 10/2013 | Mann et al. |
| 8,655,449 B2 | 2/2014 | Haller et al. |
| 2002/0039425 A1 | 4/2002 | Burnett et al. |
| 2009/0187233 A1 | 7/2009 | Stracener |
| 2010/0042183 A1 | 2/2010 | Beck |
| 2010/0317913 A1 | 12/2010 | Conn et al. |
| 2011/0116669 A1 | 5/2011 | Karunasiri |
| 2013/0018216 A1 | 1/2013 | Beckerle et al. |
| 2013/0023953 A1 | 1/2013 | Van Den Honert |
| 2013/0223664 A1 | 8/2013 | Meskens et al. |
| 2013/0238055 A1 | 9/2013 | Marnfeldt et al. |
| 2014/0350652 A1 | 11/2014 | Suwito |
| 2015/0125012 A1 | 5/2015 | Sabin |
| 2015/0224312 A1 | 8/2015 | Platz et al. |
| 2015/0374988 A1 | 12/2015 | Laudanski |
| 2015/0375003 A1 | 12/2015 | Meskens |
| 2016/0227333 A1 | 8/2016 | Babico |

OTHER PUBLICATIONS

Mazanec et al., unpublished U.S. Appl. No. 15/679,768, entitled Communication System and Methods For Fully Implantable Modular Cochlear Implant System, filed Aug. 17, 2017, 73 pages.

International Patent Application No. PCT/US2017/047354, International Search Report and Written Opinion dated Dec. 22, 2017, 25 pages.

* cited by examiner

|  | Simulated Transfer Function 1 | Simulated Transfer Function 2 | Simulated Transfer Function 3 | ... | Simulated Transfer Function m |
|---|---|---|---|---|---|
| Sound 1 | Stimulation Signal (1,1) | Stimulation Signal (1,2) | Stimulation Signal (1,3) | ... | Stimulation Signal (1,m) |
| Sound 2 | Stimulation Signal (2,1) | Stimulation Signal (2,2) | Stimulation Signal (2,3) | ... | Stimulation Signal (2,m) |
| Sound 3 | Stimulation Signal (3,1) | Stimulation Signal (3,2) | Stimulation Signal (3,3) | ... | Stimulation Signal (3,m) |
| ⋮ | ⋮ | ⋮ | ⋮ | ⋱ | ⋮ |
| Sound n | Stimulation Signal (n,1) | Stimulation Signal (n,2) | Stimulation Signal (n,3) | ... | Stimulation Signal (n,m) |

FIG. 16

|  | Programmer | Charger | Smartphone/Tablet | Smartwatch/Wearable | Fob |
|---|---|---|---|---|---|
| On/Off | X | X | X | X | X |
| Switch Profile/ Transfer Function | X | X | X | X | X |
| Adjust Volume | X | X | X | X | X |
| Adjust Mix | X | X | X | X |  |
| Receive Audio Stream | X |  | X | X |  |
| Broadcast Audio Stream | X |  | X | X |  |
| Emergency Shut-off | X | X | X | X | X |

FIG. 18

FULLY IMPLANTABLE MODULAR COCHLEAR IMPLANT SYSTEM

CROSS-REFERENCES AND PRIORITY CLAIM

This application claims priority to U.S. Provisional Patent Application No. 62/376,195 and U.S. Provisional Patent Application No. 62/376,198, each of which was filed Aug. 17, 2016, and is incorporated herein by reference in its entirety

BACKGROUND

A cochlear implant is an electronic device that may be at least partially implanted surgically into the cochlea, the hearing organ of the inner ear, to provide improved hearing to a patient. Cochlear implants may include components that are worn externally by the patient and components that are implanted internally in the patient.

External components may include a microphone, a processor, and a transmitter. Cochlear implants may detect sounds via an ear level microphone that conveys these sounds to a wearable processor. Some processors may be worn behind the patient's ear. An electronic signal from the processor may be sent to a transmission coil worn externally behind the ear over the implant. The transmission coil may send a signal to the implant receiver, located under the patient's scalp.

Internal components may include a receiver and one or more electrodes. Some cochlear implants may include additional processing circuitry among the internal components. The receiver may direct signals to one or more electrodes that have been implanted within the cochlea. The responses to these signals may then be conveyed along the auditory nerve to the cortex of the brain where they are interpreted as sound.

Some cochlear implants may be fully implanted and include a mechanism for measuring sound similar to a microphone, signal processing electronics, and means for directing signals to one or more electrodes implanted within the cochlea. Fully implanted cochlear implants typically do not include a transmission coil or a receiver coil.

Internal components of such cochlear implant systems typically require electrical power to operate. Thus, a power supply is typically included along with the other internal components. However, performance of such power supplies often degrades over time, and the power supply may require replacement. Additionally, processing circuitry technology continues to advance quickly. Improvements to processing technology over time may render the processing technology in the implanted processing circuitry outdated. Thus, there may be times when it is advantageous to replace/upgrade the processing circuitry.

However, such replacement procedures can be difficult. The location of the implanted internal components is not the most amenable to surgical procedures, and tends not to fully heal after many incisions. Additionally, replacement of some components, such as a signal processor, can require removing and reintroducing components such as electrical leads into the patient's cochlear tissue, which can be damaging to the tissue and negatively impact the efficacy of cochlear stimulation.

Additionally, different challenges exist for communicating electrical signals through a patient's body. For example, safety standards can limit the amount of current that can safely flow through a patient's body (particularly DC current). Additionally, the patient's body can act as an undesired signal path between different components within the body (e.g., via contact with the housing or "can" of each component). This can lead to reduced signal strength and/or undesired communication or interference between components. In some cases, electrical signals may even stimulate undesired regions of the patient's cochlear tissue, interfering with the efficacy of the cochlear implant.

SUMMARY

Some aspects of the disclosure are generally directed toward module cochlear implant systems. Such systems can include a cochlear electrode, a stimulator in electrical communication with the cochlear electrode, an input source, and a signal processor. The signal processor can be configured to receive an input signal from the input source and output a stimulation signal to the stimulator based on the received input signal and a transfer function of the signal processor.

In some examples, the signal processor is attached to one or both of the stimulator and the input source via a detachable connector. For example, in some embodiments, a first detachable connector can be configured to detachably connect the signal processor and the stimulator, and/or a second detachable connector can be configured to detachably connect the signal processor and the input source.

Detachably connecting the signal processor to various system components, such as an input source and/or a stimulator can enable disconnecting of the signal processor from implanted system components and removal from the wearer. This can enable replacement (e.g., upgrade) or repair of the signal processor without disturbing other implanted system components. Similarly, input sources can be detached from the signal processor for replacement, such as replacing an input communication coil receiving signals from external to the wearer to a fully-implantable input source, such as a middle ear sensor.

This disclosure is filed concurrently with the following patent applications that are owned by the owner of this disclosure: U.S. patent application Ser. No. 15/679,740, titled "COMMUNICATION SYSTEM AND METHODS FOR FULLY IMPLANTABLE MODULAR COCHLEAR IMPLANT SYSTEM," U.S. patent application Ser. No. 15/679,768, titled "COMMUNICATION SYSTEM AND METHODS FOR FULLY IMPLANTABLE MODULAR COCHLEAR IMPLANT SYSTEM," and PCT Patent Application No. PCT/US17/47354, titled "IMPLANTABLE MODULAR COCHLEAR IMPLANT SYSTEM WITH COMMUNICATION SYSTEM AND NETWORK," each of which is hereby incorporated into this disclosure by reference in its entirety.

The details of one or more examples are set forth in the accompanying drawings and the description below. Other features, objects, and advantages will be apparent from the description and drawings.

BRIEF DESCRIPTION OF THE DRAWINGS

FIG. 16 is a schematic representation of an exemplary database of pre-processed sound signals.

FIG. 18 is a chart showing the various parameters that are adjustable by each of a variety of external devices.

DETAILED DESCRIPTION

Figure 1:
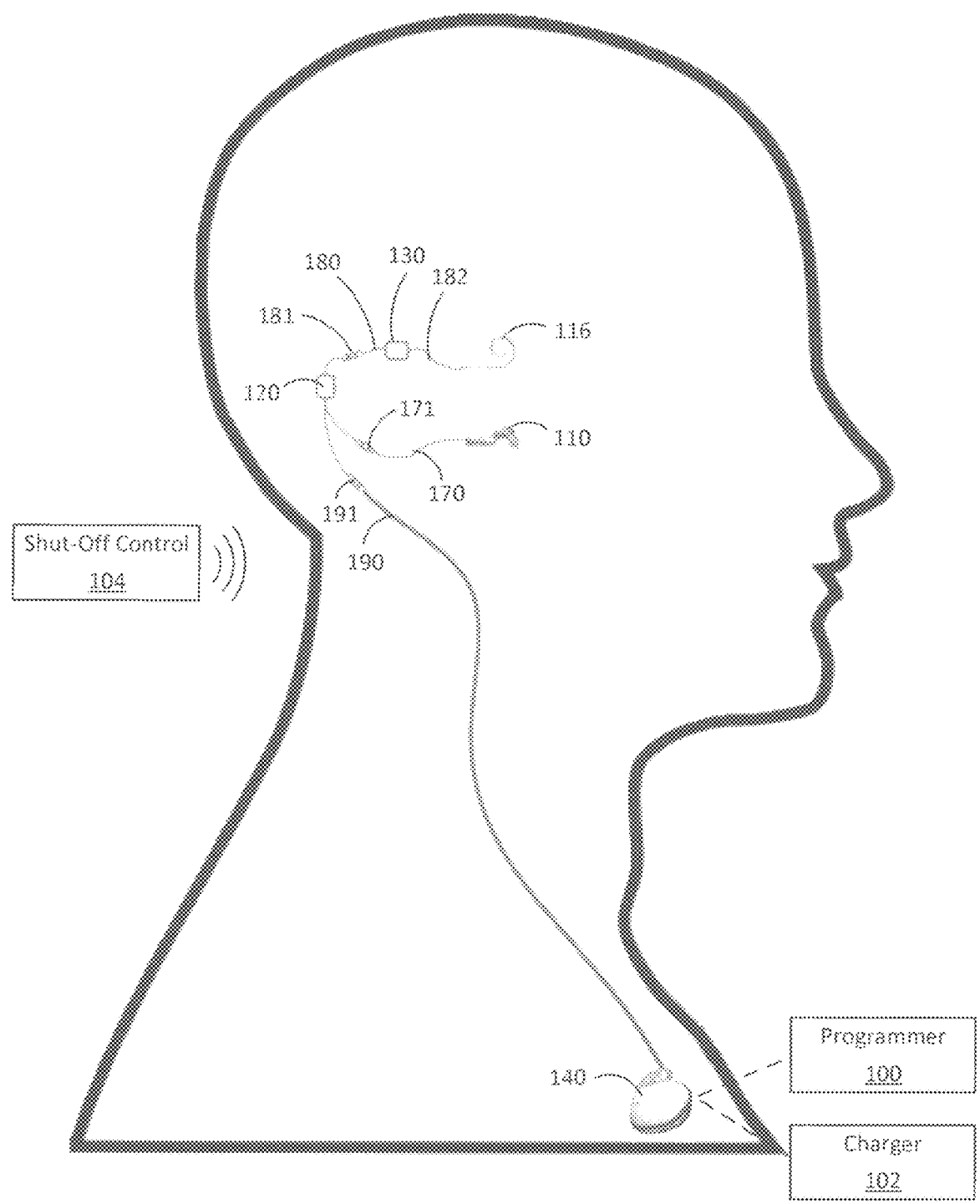
FIG. 1 shows a schematic illustration of a fully implantable cochlear implant system.

FIG. 1 shows a schematic illustration of a fully implantable cochlear implant system. The system of FIG. 1 includes a middle ear sensor 110 in communication with a signal processor 120. The middle ear sensor 110 can be configured to detect incoming sound waves, for example, using the ear structure of a patient. The signal processor 120 can be configured to receive a signal from the middle ear sensor 110 and produce an output signal based thereon. For example, the signal processor 120 can be programmed with instructions to output a certain signal based on a received signal. In some embodiments, the output of the signal processor 120 can be calculated using an equation based on received input signals. Alternatively, in some embodiments, the output of the signal processor 120 can be based on a lookup table or other programmed (e.g., in memory) correspondence between the input signal from the middle ear sensor 110 and the output signal. While not necessarily based explicitly on a function, the relationship between the input to the signal processor 120 (e.g., from the middle ear sensor 110) and the output of the signal processor 120 is referred to as the transfer function of the signal processor 120.

The system of FIG. 1 further includes a cochlear electrode 116 implanted into the cochlear tissues of a patient. The cochlear electrode 116 is in electrical communication with an electrical stimulator 130, which can be configured to provide electrical signals to the cochlear electrode 116 in response to input signals received by the electrical stimulator 130. In some examples, the cochlear electrode 116 is fixedly attached to the electrical stimulator 130. In other examples, the cochlear electrode 116 is removably attached to the electrical stimulator 130. As shown, the electrical stimulator 130 is in communication with the signal processor 120. In some embodiments, the electrical stimulator 130 provides electrical signals to the cochlear electrode 116 based on output signals from the signal processor 120.

In various embodiments, the cochlear electrode 116 can include any number of contact electrodes in electrical contact with different parts of the cochlear tissue. In such embodiments, the electrical stimulator 130 can be configured to provide electrical signals to any number of such contact electrodes to stimulate the cochlear tissue. For example, in some embodiments, the electrical stimulator 130 is configured to activate different contact electrodes or combinations of contact electrodes of the cochlear electrode 116 in response to different input signals received from the signal processor 120. This can help the patient differentiate between different input signals.

During exemplary operation, the middle ear sensor 110 detects audio signals, for example, using features of the patient's ear anatomy as described elsewhere herein and in U.S. Patent Publication No. 2013/0018216, which is hereby incorporated by reference in its entirety. The signal processor 120 can receive such signals from the middle ear sensor 110 and produce an output to the electrical stimulator 130 based on the transfer function of the signal processor 120. The electrical stimulator 130 can then stimulate one or more contact electrodes of the cochlear electrode 116 based on the received signals from the signal processor 120.

Figure 2:
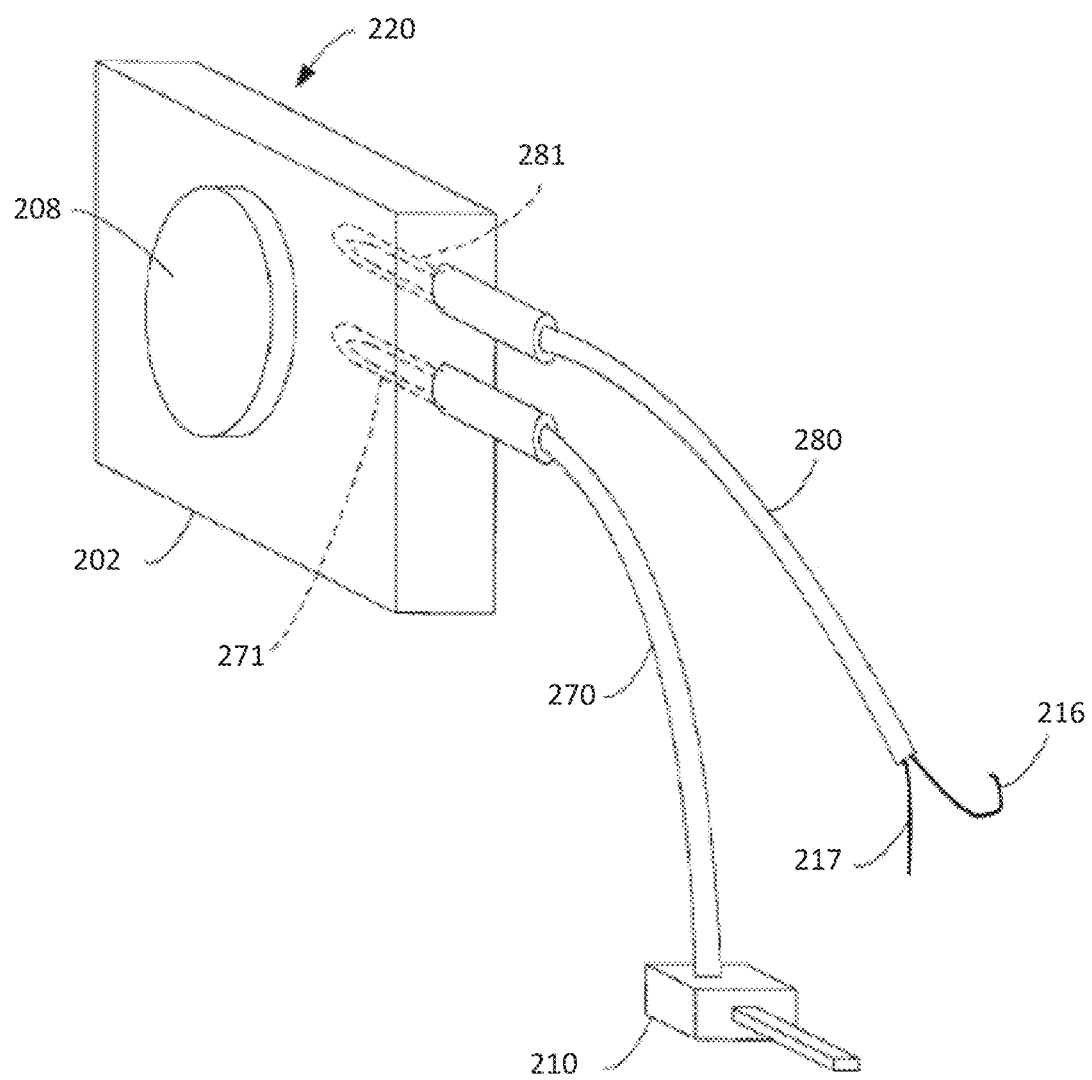
FIG. 2 shows an embodiment of a fully-implantable cochlear implant.

Referring to FIG. 2, an embodiment of a fully-implantable cochlear implant is shown. The device in this embodiment includes a processor 220 (e.g., signal processor), a sensor 210, a first lead 270 connecting the sensor 210 to the processor 220, and a combination lead 280 attached to the processor 220, wherein combination lead 280 contains both a ground electrode 217 and a cochlear electrode 216. The illustrated processor 220 includes a housing 202, a coil 208, first female receptacle 271 and second female receptacle 281 for insertion of the leads 270 and 280, respectively.

In some embodiments, coil 208 can receive power and/or data from an external device, for instance, including a transmission coil (not shown). Some such examples are described in U.S. Patent Publication No. 2013/0018216, which is incorporated by reference. In other examples, processor 220 is configured to receive power and/or data from other sources, such as an implantable battery and/or communication module as shown in FIG. 1. Such battery and/or communication module can be implanted, for example, into the pectoral region of the patient in order to provide adequate room for larger equipment (e.g., a relatively large battery) for prolonged operation (e.g., longer battery life). Additionally, in the event a battery needs eventual replacement, a replacement procedure in the patient's pectoral region can be performed several times without certain vascularization issues that can arise near the location of the cochlear implant. For example, in some cases, repeated procedures (e.g., battery replacement) near the cochlear implant can result in a decreased ability for the skin in the region to heal after a procedure. Placing a replaceable component such as a battery in the pectoral region can facilitate replacement procedures with reduced risk for such issues.

Figure 3A:
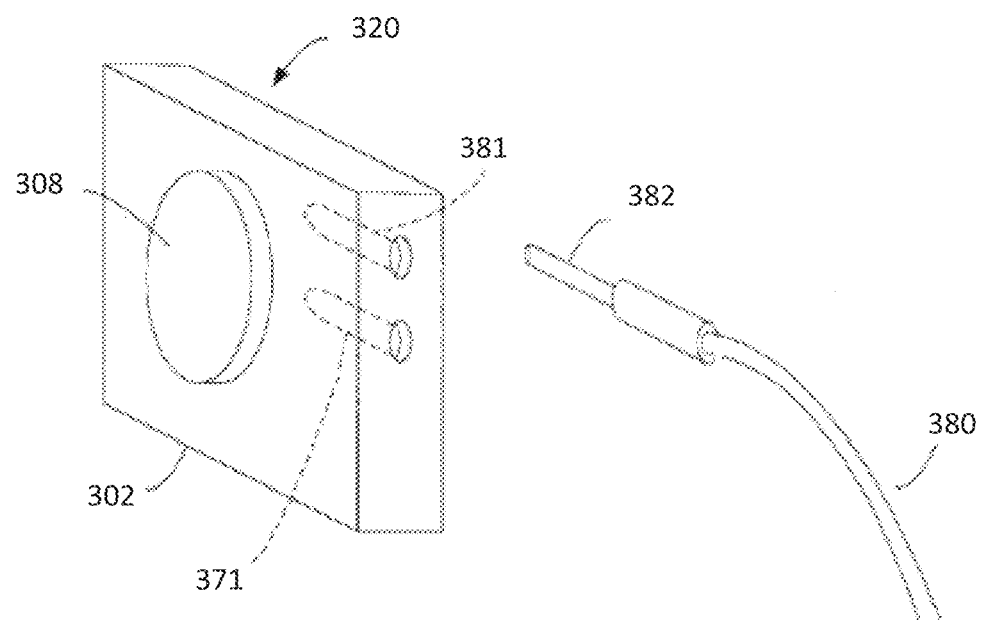
FIGS. 3A and 3B are exemplary illustrations showing communication with the signal processor.
Figure 3B:
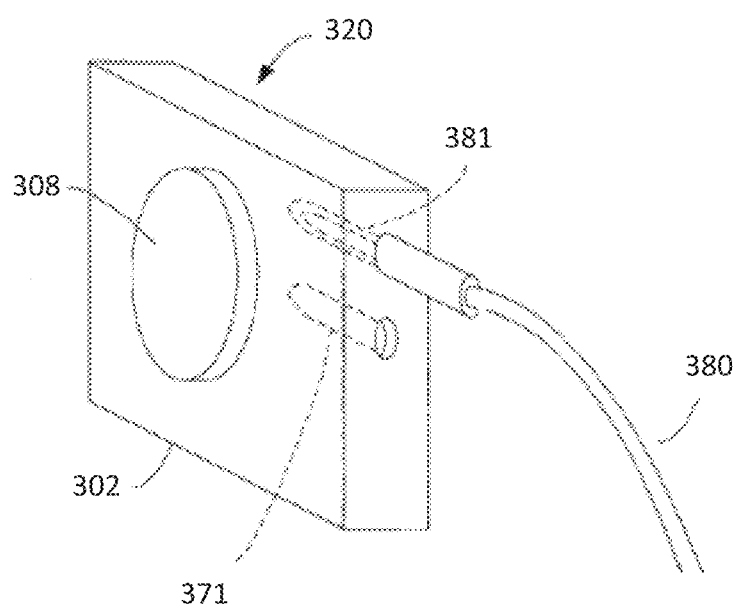

FIGS. 3A and 3B are exemplary illustrations showing communication with a signal processor. For example, referring to FIGS. 3A and 3B, the processor 320, includes a housing 302, a coil 308, and a generic lead 380 are shown. The lead 380 is removable and can be attached to the processor 320 by insertion of a male connector 382 of the generic lead 380 into any available female receptacle, shown here as 371 or 381. FIG. 3A shows the processor 320 with the generic lead 380 removed. FIG. 3B shows the processor 320 with the generic lead 380 attached. The male connector 382 is exchangeable, and acts as a seal to prevent or minimize fluid transfer into the processor 320.

Figure 4:
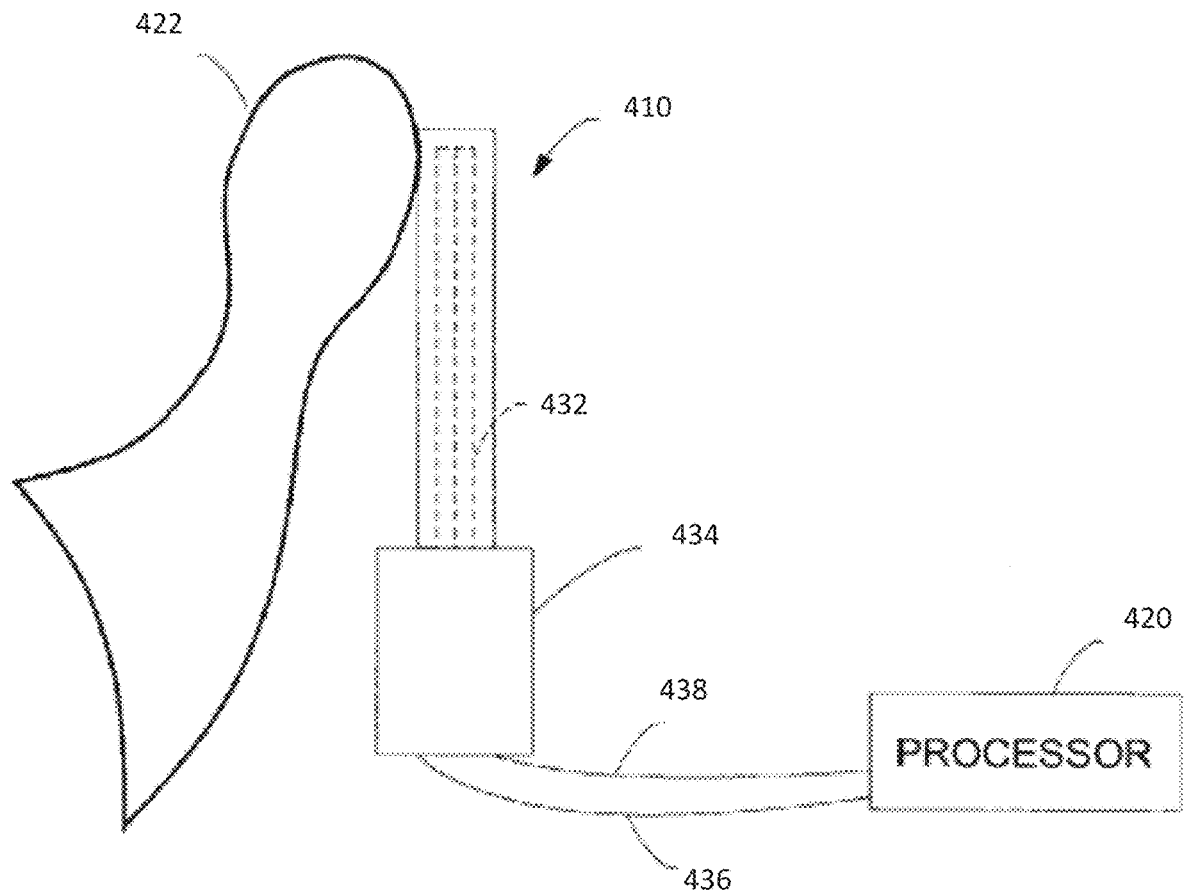
FIGS. 4 and 5 illustrate embodiments of an exemplary middle ear sensor for use in conjunction with anatomical features of a patient.
Figure 5:
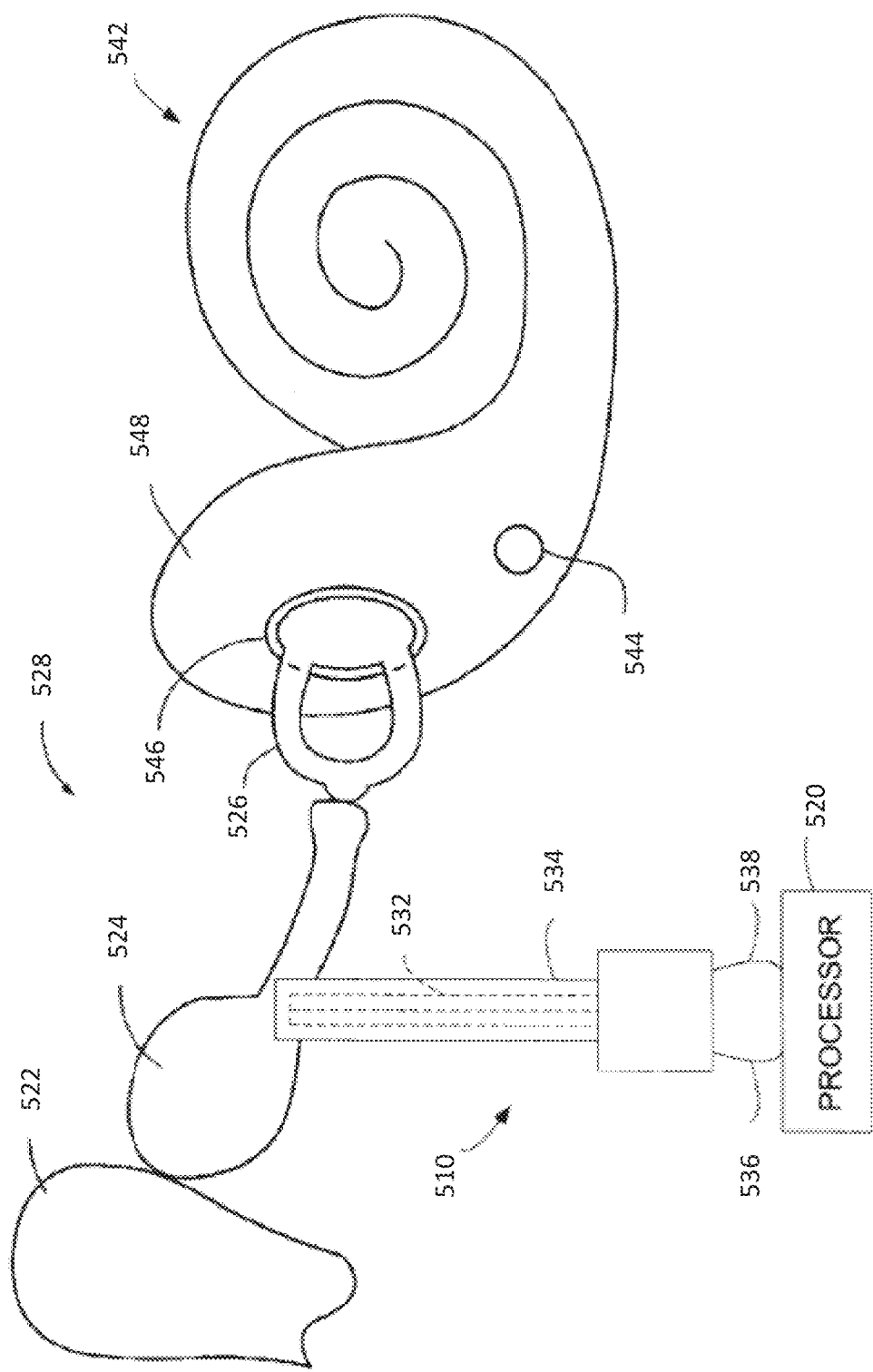

FIGS. 4 and 5 illustrate embodiments of an exemplary middle ear sensor for use in conjunction with anatomical features of a patient. Referring to FIG. 4, an embodiment of the sensor 410 of a fully-implantable cochlear implant is shown. Here, the sensor 410 is touching the malleus 422. The sensor may include a cantilever 432 within a sensor housing 434. The sensor 410 may be in communication with the processor 420 by at least two wires 436 and 438, which may form a first lead (e.g., 270). Both wires can be made of biocompatible materials, but need not necessarily be the same biocompatible material. Examples of such biocompatible materials can include tungsten, platinum, palladium, and the like. In various embodiments, one, both, or neither of wires 436 and 438 are coated with a coating and/or disposed inside a casing, such as described in U.S. Patent Publication No. 2013/0018216, which is incorporated by reference.

The illustrated cantilever 432 includes at least two ends, where at least one end is in operative contact with the tympanic membrane or one or more bones of the ossicular chain. The cantilever 432 may be a laminate of at least two layers of material. The material used may be piezoelectric. One example of such a cantilever 432 is a piezoelectric bimorph, which is well-known in the art (see for example, U.S. Pat. No. 5,762,583). In one embodiment, the cantilever is made of two layers of piezoelectric material. In another embodiment, the cantilever is made of more than two layers of piezoelectric material. In yet another embodiment, the cantilever is made of more than two layers of piezoelectric material and non-piezoelectric material.

The sensor housing 434 of the sensor 410 may be made of a biocompatible material. In one embodiment, the biocompatible material may be titanium or gold. In another embodiment, the sensor 410 may be similar to the sensor described in U.S. Pat. No. 7,524,278 to Madsen et al., or available sensors, such as that used in the ESTEEM™ implant (Envoy Medical, Corp., St. Paul, Minn.), for example. In alternative embodiments, the sensor 410 may be an electromagnetic sensor, an optical sensor, or an accelerometer. Accelerometers are known in the art, for example, as described in U.S. Pat. No. 5,540,095.

Referring to FIG. 5, an embodiment of the sensor 510 of a fully-implantable cochlear implant is shown. Also shown are portions of the subject's anatomy, which includes, if the subject is anatomically normal, at least the malleus 522, incus 524, and stapes 526 of the middle ear 528, and the cochlea 548, oval window 546, and round window 544 of the inner ear 542. Here, the sensor 510 is touching the incus 524. The sensor 510 in this embodiment can be as described for the embodiment of sensor 410 shown in FIG. 4. Further, although not shown in a drawing, the sensor 510 may be in operative contact with the tympanic membrane or the stapes, or any combination of the tympanic membrane, malleus 522, incus 524, or stapes 526.

FIGS. 4 and 5 illustrate an exemplary middle ear sensor for use with systems described herein. However, other middle ear sensors can be used, such as sensors using microphones or other sensors capable of receiving an input corresponding to detected sound and outputting a corresponding signal to the signal processor. Additionally or alternatively, systems can include other sensors configured to output a signal representative of sound received at or near a user's ear, such as a microphone or other acoustic pickup located in the user's outer ear or implanted under the user's skin. Such devices may function as an input source, for example, to the signal processor such that the signal processor receives an input signal from the input source and generates and output one or more stimulation signals according to the received input signal and the signal processor transfer function.

Referring back to FIG. 1, the signal processor 120 is shown as being in communication with the middle ear sensor 110, the electrical stimulator 130, and the implantable battery and/or communication module 140. As described elsewhere herein, the signal processor 120 can receive input signals from the middle ear sensor 110 and/or other input source(s) and output signals to the electrical stimulator 130 for stimulating the cochlear electrode 116. The signal processor 120 can receive data (e.g., processing data establishing or updating the transfer function of the signal processor 120) and/or power from the implantable battery and/or communication module 140. In some embodiments, the signal processor 120 can communicate with such components via inputs such as those shown in FIG. 3.

In some embodiments, the implantable battery and/or communication module 140 can communicate with external components, such as a programmer 100 and/or a battery charger 102. The battery charger 102 can wirelessly charge the battery in the implantable battery and/or communication module 140 when brought into proximity with the implantable battery and/or communication module 140 in the pectoral region of the patient. Such charging can be accomplished, for example, using inductive charging. The programmer 100 can be configured to wirelessly communicate with the implantable battery and/or communication module 140 via any appropriate wireless communication technology, such as Bluetooth, Wi-Fi, and the like. In some examples, the programmer 100 can be used to update the system firmware and/or software. In an exemplary operation, the programmer 100 can be used to communicate an updated signal processor 120 transfer function to the implantable battery and/or communication module 140. In various embodiments, the programmer 100 and charger 102 can be separate devices or can be integrated into a single device.

In the illustrated example of FIG. 1, the signal processor 120 is connected to the middle ear sensor 110 via lead 170. In some embodiments, lead 170 can provide communication between the signal processor 120 and the middle ear sensor 110. In some embodiments, lead 170 can include a plurality of isolated conductors providing a plurality of communication channels between the middle ear sensor 110 and the signal processor 120. The lead 170 can include a coating such as an electrically insulating sheath to minimize any conduction of electrical signals to the body of the patient.

Figure 6:
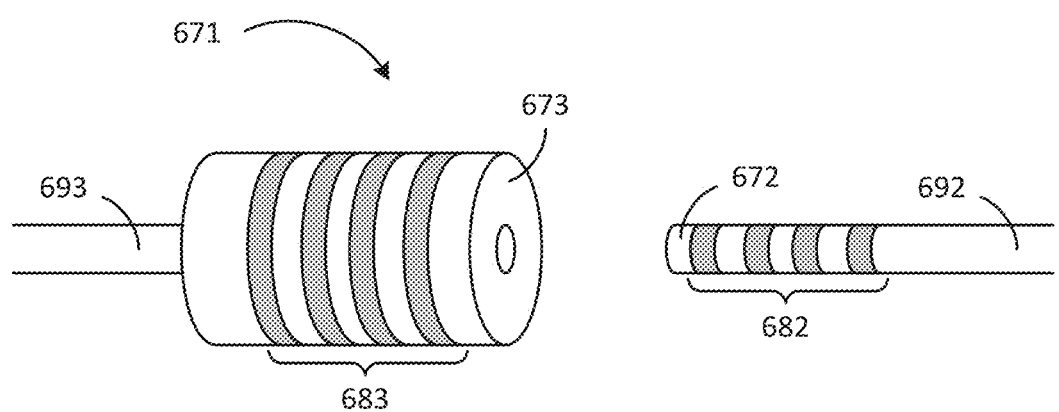
FIG. 6 shows an illustration of an exemplary detachable connector.

In various embodiments, one or more communication leads can be detachable such that communication between two components can be disconnected in order to electrically and/or mechanically separate such components. For instance, in some embodiments, lead 170 includes a detachable connector 171. Detachable connector 171 can facilitate decoupling of the signal processor 120 and middle ear sensor 110. FIG. 6 shows an illustration of an exemplary detachable connector. In the illustrated example, the detachable connector 671 includes a male connector 672 and a female connector 673. In the illustrated example, the male connector 672 includes a plurality of isolated electrical contacts 682 and female connector 673 includes a corresponding plurality of electrical contacts 683. When the male connector 672 is inserted into the female connector 673, contacts 682 make electrical contact with contacts 683. Each corresponding pair of contacts 682, 683 can provide a separate channel of communication between components connected via the detachable connector 671. In the illustrated example, four channels of communication are possible, but it will be appreciated that any number of communication channels are possible. Additionally, while shown as individual circumferentially extending contacts 683, other configurations are possible.

In some embodiments, male 672 and female 673 connectors are attached at the end of leads 692, 693, respectively. Such leads can extend from components of the implantable cochlear system. For example, with reference to FIG. 1, in some embodiments, lead 170 can include a first lead extending from the middle ear sensor 110 having one of a male (e.g., 672) or a female (e.g., 673) connector and a second lead extending from the signal processor 120 having the other of the male or female connector. The first and second leads can be connected at detachable connector 171 in order to facilitate communication between the middle ear sensor 110 and the signal processor 120.

In other examples, a part of the detachable connector 171 can be integrated into one of the middle ear sensor 110 and the signal processor 120 (e.g., as shown in FIG. 3). For example, in an exemplary embodiment, the signal processor 120 can include a female connector (e.g., 673) integrated into a housing of the signal processor 120. Lead 170 can extend fully from the middle ear sensor 110 and terminate at a corresponding male connector (e.g., 672) for inserting into the female connector of the signal processor 120. In still further embodiments, a lead (e.g., 170) can include connectors on each end configured to detachably connect with connectors integrated into each of the components in communication. For example, lead 170 can include two male connectors, two female connectors, or one male and one female connector for detachably connecting with corresponding connectors integral to the middle ear sensor 110 and the signal processor 120. Thus, lead 170 may include two or more detachable connectors.

Similar communication configurations can be established for detachable connector 181 of lead 180 facilitating communication between the signal processor 120 and the stimulator 130 and for detachable connector 191 of lead 190 facilitating communication between the signal processor 120 and the implantable battery and/or communication module 140. Leads (170, 180, 190) can include pairs of leads having corresponding connectors extending from each piece of communicating equipment, or connectors can be built in to any one or more communicating components.

In such configurations, each of the electrical stimulator 130, signal processor 120, middle ear sensor 110, and battery and/or communication module can each be enclosed in a housing, such as a hermetically sealed housing comprising biocompatible materials. Such components can include feedthroughs providing communication to internal components enclosed in the housing. Feedthroughs can provide electrical communication to the component via leads extending from the housing and/or connectors integrated into the components.

In a module configuration such as that shown in FIG. 1, various components can be accessed (e.g., for upgrades, repair, replacement, etc.) individually from other components. For example, as signal processor 120 technology improves (e.g., improvements in size, processing speed, power consumption, etc.), the signal processor 120 implanted as part of the system can be removed and replaced independently of other components. In an exemplary procedure, an implanted signal processor 120 can be disconnected from the electrical stimulator 130 by disconnecting detachable connector 181, from the middle ear sensor 110 by disconnecting detachable connector 171, and from the implantable battery and/or communication module 140 by disconnecting detachable connector 191. Thus, the signal processor 120 can be removed from the patient while other components such as the electrical stimulator 130, cochlear electrode 116, middle ear sensor 110, and battery and/or communication module can remain in place in the patient.

After the old signal processor is removed, a new signal processor can be connected to the electrical stimulator 130, middle ear sensor 110, and implantable battery and/or communication module 140 via detachable connectors 181, 171, and 191, respectively. Thus, the signal processor (e.g., 120) can be replaced, repaired, upgraded, or any combination thereof, without affecting the other system components. This can reduce, among other things, the risk, complexity, duration, and recovery time of such a procedure. In particular, the cochlear electrode 116 can be left in place in the patient's cochlea while other system components can be adjusted, reducing trauma to the patient's cochlear tissue.

Such modularity of system components can be particularly advantageous when replacing a signal processor 120, such as described above. Processor technology continues to improve, and will likely continue to markedly improve in the future, making the signal processor 120 a likely candidate for significant upgrades and/or replacement during the patient's lifetime. Additionally, in embodiments such as the embodiment shown in FIG. 1, the signal processor 120 communicates with many system components. For example, as shown, the signal processor 120 is in communication with each of the electrical stimulator 130, the middle ear sensor 110, and the implantable battery and/or communication module 140. Detachably connecting such components with the signal processor 120 (e.g., via detachable connectors 181, 171, and 191) enables replacement of the signal processor 120 without disturbing any other components. Thus, in the event of an available signal processor 120 upgrade and/or a failure of the signal processor 120, the signal processor 120 can be disconnected from other system components and removed.

While many advantages exist for a replaceable signal processor 120, the modularity of other system components can be similarly advantageous, for example, for upgrading any system component. Similarly, if a system component (e.g., the middle ear sensor 110) should fail, the component can be disconnected from the rest of the system (e.g., via detachable connector 171) and replaced without disturbing the remaining system components. In another example, even a rechargeable battery included in the implantable battery and/or communication module 140 may eventually wear out and need replacement. The implantable battery and/or communication module 140 can be replaced or accessed (e.g., for replacing the battery) without disturbing other system components. Further, as discussed elsewhere herein, when the implantable battery and/or communication module 140 is implanted in the pectoral region of the patient, such as in the illustrated example, such a procedure can leave the patient's head untouched, eliminating unnecessarily frequent access beneath the skin.

While various components are described herein as being detachable, in various embodiments, one or more components configured to communicate with one another can be integrated into a single housing. For example, in some embodiments, signal processor 120 can be integrally formed with the stimulator 130 and cochlear electrode 116. For example, in an exemplary embodiment, processing and stimulation circuitry of a signal processor 120 and stimulator 130 can be integrally formed as a single unit in a housing coupled to a cochlear electrode. Cochlear electrode and the signal processor/stimulator can be implanted during an initial procedure and operate as a single unit.

In some embodiments, while the integral signal processor/stimulator/cochlear electrode component does not get removed from a patient due to potential damage to the cochlear tissue into which the cochlear electrode is implanted, system upgrades are still possible. For example, in some embodiments, a module signal processor may be implanted alongside the integral signal processor/stimulator component and communicate therewith. In some such examples, the integral signal processor may include a built-in bypass to allow a later-implanted signal processor to interface directly with the stimulator. Additionally or alternatively, the modular signal processor can communicate with the integral signal processor, which may be programmed with a unity transfer function. Thus, in some such embodiments, signals from the modular signal processor may be essentially passed through the integral signal processor unchanged so that the modular signal processor effectively controls action of the integral stimulator. Thus, in various embodiments, hardware and/or software solutions exist for upgrading an integrally attached signal processor that may be difficult or dangerous to remove.

Figure 7:
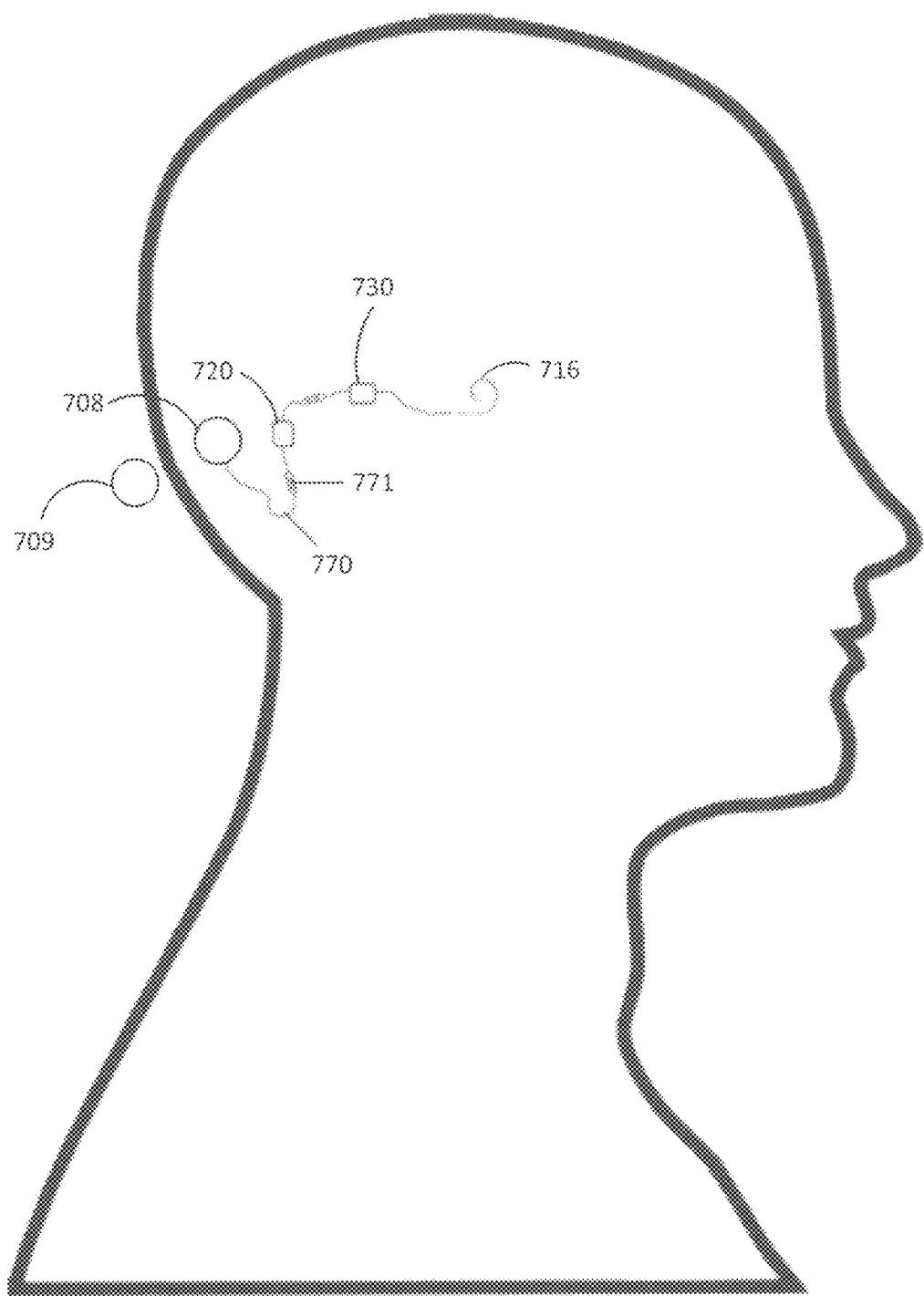
FIG. 7 shows an exemplary cochlear implant system in a patient that is not fully physically developed, such as a child.

Another advantage to a modular cochlear implant system such as shown in FIG. 1 is the ability to implant different system components into a patient at different times. For example, infants and children are typically not suited for a fully implantable system such as shown in FIG. 1. Instead, such patients typically are candidates to wear a traditional cochlear implant system. For example, FIG. 7 shows an exemplary cochlear implant system in a patient that is not fully physically developed, such as a child. The system includes a cochlear electrode 716 implanted into the cochlear tissue of the patient. The cochlear electrode 716 of FIG. 7 can include many of the properties of the cochlear electrodes described herein. The cochlear electrode 716 can be in electrical communication with an electrical stimulator 730, which can be configured to stimulate portions of the cochlear electrode 716 in response to an input signal, such as described elsewhere herein. The electrical stimulator 730 can receive input signals from a signal processor 720.

In some cases, components such as a middle ear sensor are incompatible with a patient who is not fully physically developed. For example, various dimensions within a growing patient's anatomy, such as spacing between anatomical structures or between locations on anatomical structures (e.g., equipment attachment points) may change as the patient grows, thereby potentially rendering a middle ear sensor that is extremely sensitive to motion ineffective. Similarly, the undeveloped patient may not be able to support the implantable battery and/or communication module. Thus, the signal processor 720 can be in communication with a communication device for communicating with components external to the patient. Such communication components can include, for example, a coil 708, shown as being connected to the signal processor 720 via lead 770. The coil 708 can be used to receive data and/or power from devices external to the user. For example, microphone or other audio sensing device (not shown) can be in communication with an external coil 709 configured to transmit data to the coil 708 implanted in the patient. Similarly, a power source (e.g., a battery) can be coupled to an external coil 709 and configured to provide power to the implanted components via the implanted coil 708. Additionally, processing data (e.g., updates to the signal processor 720 transfer function) can also be communicated to the implanted coil 708 from an external coil 709. While generally discussed using coil 708, it will be appreciated that communication between external and implanted components (e.g., the signal processor 720) can be performed using other communication technology, such as various forms of wireless communication. As shown, in the embodiment of FIG. 7, the signal processor 720 is coupled to the coil 708 via lead 770 and detachable connector 771. Accordingly, the coil 708 can be detached from the signal processor 720 and removed without disrupting the signal processor 720.

When a patient has become fully developed, for example, to the point that the patient can safely accommodate a middle ear sensor and an implantable battery and/or communication module, the coil 708 can be removed and remaining components of the fully implantable system can be implanted. That is, once a patient is developed, the cochlear implant system (e.g., of FIG. 7) can be updated to a fully implantable cochlear implant system (e.g., of FIG. 1). In some examples, the patient is considered sufficiently developed once the patient reaches age 18 or another predetermined age. Additional or alternative criteria may be used, such as when various anatomical sizes or determined developmental states are achieved.

Figure 8:
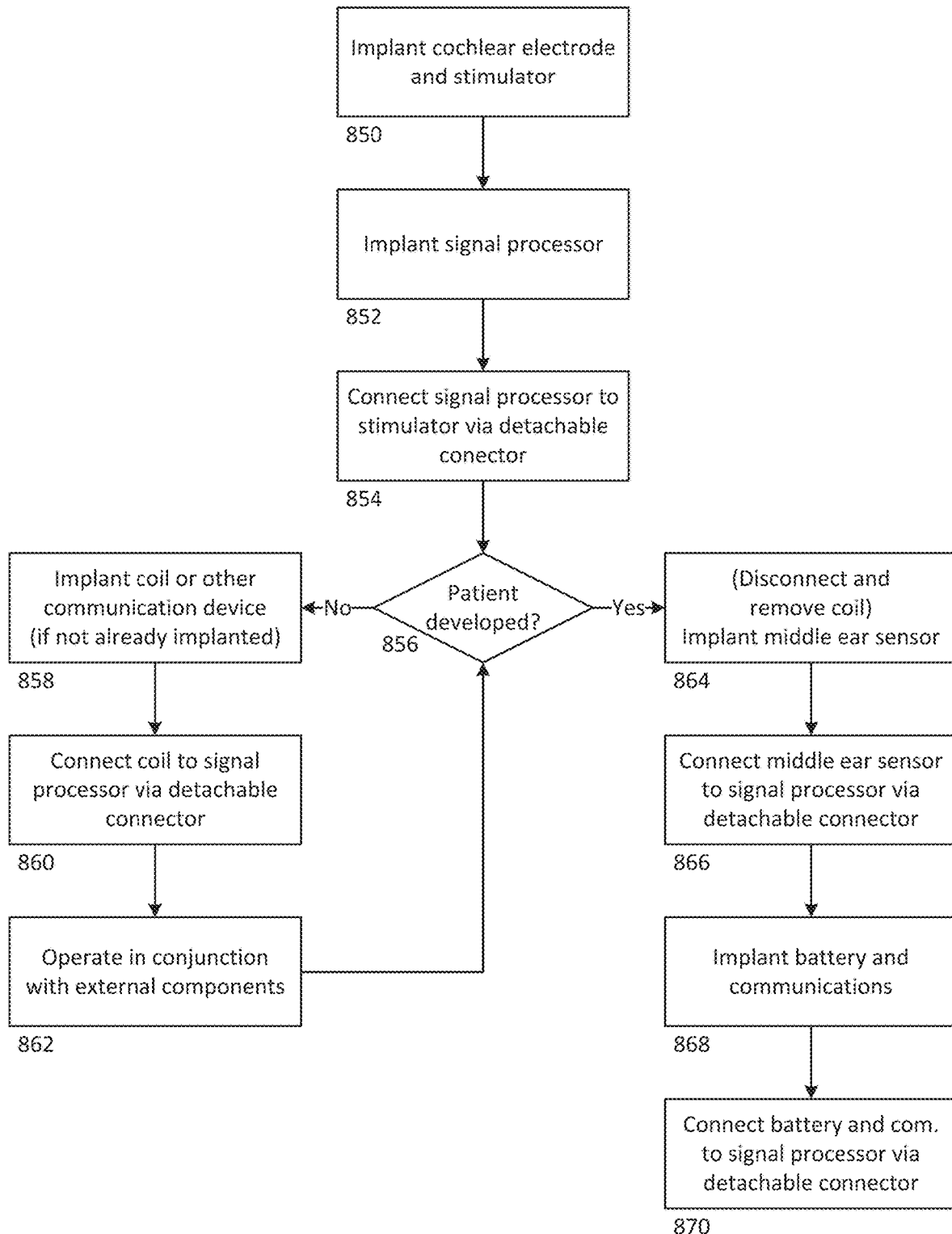
FIG. 8 is a process-flow diagram illustrating an exemplary process for installing and/or updating an implantable cochlear implant system into a patient.

FIG. 8 is a process-flow diagram illustrating an exemplary process for installing and/or updating an implantable cochlear implant system into a patient. A cochlear electrode can be implanted in communication with the patient's cochlear tissue and an electrical stimulator can be implanted in communication with the cochlear electrode (850). A signal processor can be implanted into the patient (852). As described elsewhere herein, the signal processor can be connected to the electrical stimulator via a detachable connector (854). In examples in which the signal processor is integrally formed with one or more components, such as the stimulator and cochlear electrode, steps 850, 852, and 854 can be combined into a single step comprising implanting the cochlear electrode, stimulator, and signal processor component.

If, at the time of implementing the process of FIG. 8, it can be determined if the patient is considered sufficiently developed (856). If not, a coil (or other communication device) such as described with respect to FIG. 7 can be implanted (858). The coil can be connected to the signal processor via the detachable connector (860), and the cochlear implant can operate in conjunction with external components (862), such as microphones and external power supplies and coils.

However, if a patient is, or has become, sufficiently developed (856), additional components can be implanted into the patient. For example, the method can include implanting a middle ear sensor (864) and connecting the middle ear sensor to the signal processor via a detachable connector (866). Additionally, the method can include implanting a battery and/or communication module (868) and connecting the battery and/or communication module to the signal processor via a detachable connector (870). If the patient had become sufficiently developed after having worn a partially external device such as that described with respect to FIG. 7 and steps 858-862, the method can include removing various components that had been previously implanted. For example, a coil, such as implanted in step 858, can be disconnected and removed during the procedure of implanting the middle ear sensor (864).

The process of FIG. 8 can be embodied in a method of fitting a patient with an implantable hearing system. Such a method can include implanting a first system (e.g., the system of FIG. 7) into a patient at a first age. This can include, for example, performing steps 850-562 in FIG. 8. The method can further include, when the patient reaches a second age, the second age being greater than the first, removing some components of the first system (e.g., a coil) and implanting the not-yet implanted components of second system (e.g., the system of FIG. 1), for example, via steps 864-870 of FIG. 8.

Transitioning from the system of FIG. 7 to the system of FIG. 1, for example, via the process of FIG. 8, can have several advantages. From a patient preference standpoint, some patients may prefer a system that is totally implanted and requires no wearable external components. Additionally, an implanted battery and/or communication module in communication with the signal processor via lead 190 (and detachable connector 191) can much more efficiently relay power and/or data to the signal processor when compared to an external device such as a coil.

Such modular systems provide distinct advantages over previous implantable or partially implantable cochlear implant systems. Generally, previous systems include several components included into a single housing implanted into the patient. For example, functionality of a signal processor, electrical stimulator, and sensor can be enclosed in a single, complex component. If any such aspects of the component fail, which becomes more likely as the complexity increases, the entire module must be replaced. By contrast, in a modular system, such as shown in FIG. 1, individual components can be replaced while leaving others in place. Additionally, such systems including, for example, coil-to-coil power and/or data communication through the patient's skin also generally communicate less efficiently than an internal connection such as via the lead 190. Modular systems such as shown in FIGS. 1 and 7 also allow for a smooth transition from a partially implantable system for a patient who is not yet fully developed and a fully implantable system once the patient has become fully developed.

While often described herein as using an electrical stimulator to stimulate the patient's cochlear tissue via a cochlear electrode, in some examples, the system can additionally or alternatively include an acoustic stimulator. An acoustic stimulator can include, for example, a transducer (e.g., a piezoelectric transducer) configured to provide mechanical stimulation to the patient's ear structure. In an exemplary embodiment, the acoustic stimulator can be configured to stimulate one or more portions of the patient's ossicular chain via amplified vibrations. Acoustic stimulators can include any appropriate acoustic stimulators, such as those found in the ESTEEM™ implant (Envoy Medical Corp., St. Paul, Minn.) or as described in U.S. Pat. Nos. 4,729,366, 4,850,962, and 7,524,278, and U.S. Patent Publication No. 20100042183, each of which is incorporated herein by reference in its entirety.

Figure 9:
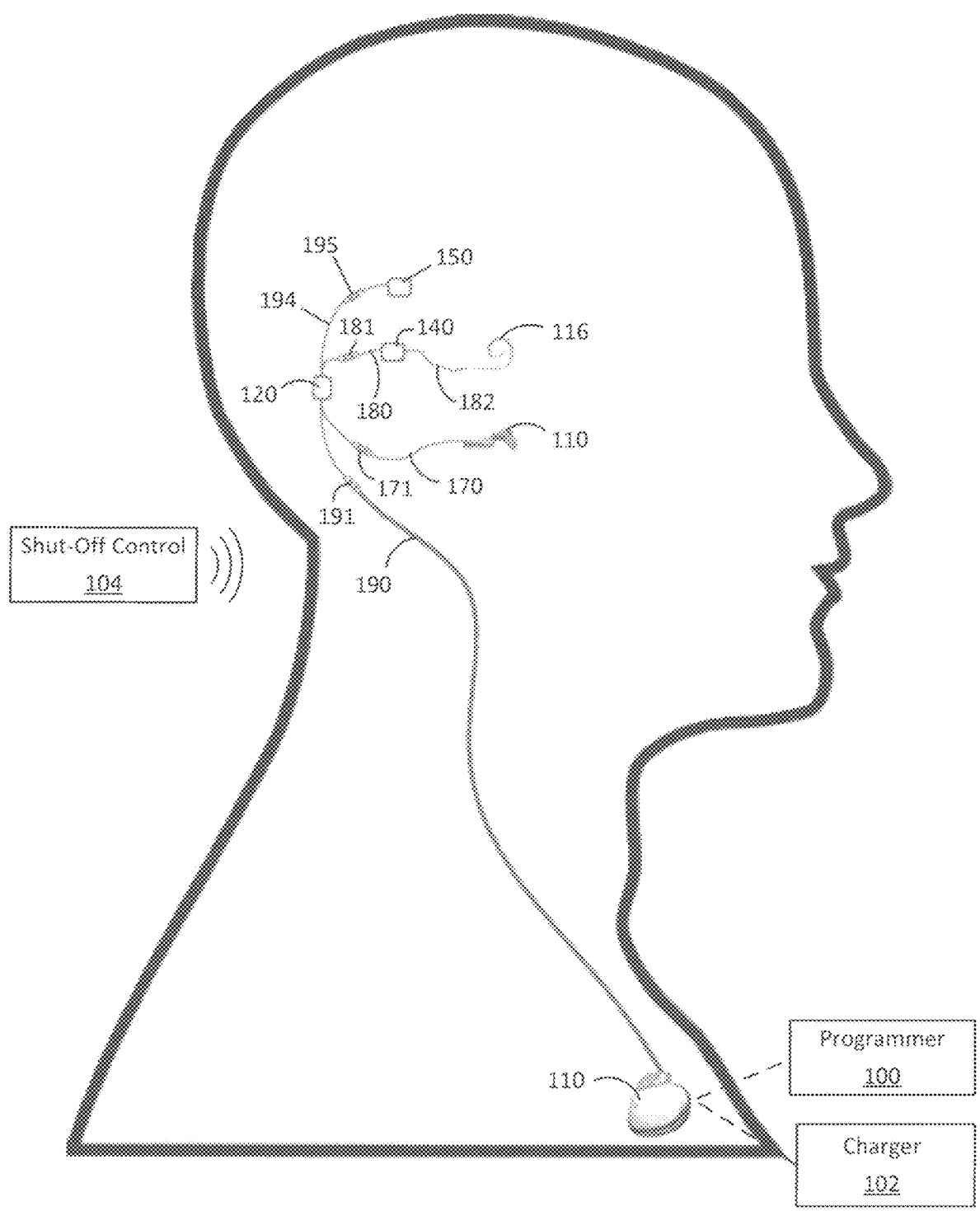
FIG. 9 is a schematic diagram illustrating an exemplary implantable system including an acoustic stimulator.

FIG. 9 is a schematic diagram illustrating an exemplary implantable system including an acoustic stimulator. The acoustic stimulator can be implanted proximate the patient's ossicular chain and can be in communication with a signal processor via lead 194 and detachable connector 195. The signal processor can behave as described elsewhere herein, and can be configured to cause acoustic stimulation of the ossicular chain via the acoustic stimulator in in response to input signals from the middle ear sensor according to a transfer function of the signal processor.

The acoustic stimulator of FIG. 9 can be used similarly to the electrical stimulator as described elsewhere herein. For instance, an acoustic stimulator can be mechanically coupled to a patient's ossicular chain upon implanting the system, and coupled to the signal processor via lead 194 and detachable connector 195. Similarly to systems described elsewhere herein with respect to the electrical stimulator, if the signal processor requires replacement or repair, the signal processor can be disconnected from the acoustic stimulator (via detachable connector 195) so that the signal processor can be removed without disturbing the acoustic stimulator.

In general, systems incorporating an acoustic sensor such as shown in FIG. 9 can operate in the same way as systems described elsewhere herein employing an electrical stimulator and cochlear electrode only substituting electrical stimulation for acoustic stimulation. The same modularity benefits, including system maintenance and upgrades as well as the ability to convert to a fully implantable system when a patient becomes sufficiently developed, can be similarly realized using acoustic stimulation systems. For example, the process illustrated in FIG. 8 can be performed in an acoustic stimulation system simply by substituting the electrical stimulator and cochlear electrode for an acoustic stimulator.

Some systems can include a hybrid system comprising both an electrical stimulator and an acoustic stimulator in communication with the signal processor. In some such examples, the signal processor can be configured to stimulate electrically and/or acoustically according to the transfer function of the signal processor. In some examples, the type of stimulation used can depend on the input signal received by the signal processor. For instance, in an exemplary embodiment, the frequency content of the input signal to the signal processor can dictate the type of stimulation. In some cases, frequencies below a threshold frequency could be represented using one of electrical and acoustic stimulation while frequencies above the threshold frequency could be represented using the other of electrical and acoustic stimulation. Such a threshold frequency could be adjustable based on the hearing profile of the patient. Using a limited range of frequencies can reduce the number of frequency domains, and thus the number of contact electrodes, on the cochlear electrode. In other examples, rather than a single threshold frequency defining which frequencies are stimulated electrically and acoustically, various frequencies can be stimulated both electrically and acoustically. In some such examples, the relative amount of electrical and acoustic stimulation can be frequency-dependent. As described elsewhere herein, the signal processor transfer function can be updated to meet the needs of the patient, including the electrical and acoustic stimulation profiles.

With further reference to FIGS. 1 and 9, in some examples, a system can include a shut-off controller 104, which can be configured to wirelessly stop an electrical stimulator 130 from stimulating the patient's cochlear tissue and/or an acoustic stimulator 150 from stimulating the patient's ossicular chain. For example, if the system is malfunctioning or an uncomfortably loud input sound causes an undesirable level of stimulation, the user may use the shut-off controller 104 to cease stimulation from the stimulator 130. The shut-off controller 104 can be embodied in a variety of ways. For example, in some embodiments, the shut-off controller 104 can be integrated into other external components, such as the programmer 100. In some such examples, the programmer 100 includes a user interface by which a user can select an emergency shut-off feature to cease stimulation. Additionally or alternatively, the shut-off controller 104 can be embodied as a separate component. This can be useful in situations in which the patient may not have immediate access to the programmer 100. For example, the shut-off controller 104 can be implemented as a wearable component that the patient can wear at all or most times, such as a ring, bracelet, necklace, or the like.

The shut-off controller 104 can communicate with the system in order to stop stimulation in a variety of ways. In some examples, the shut-off controller 104 comprises a magnet that is detectable by a sensor (e.g., a Hall-Effect sensor) implanted in the patient, such as in the processor and/or the implantable battery and/or communication module 140. In some such embodiments, when the magnet is brought sufficiently close to the sensor, the system can stop stimulation of the cochlear tissue or ossicular chain.

After the shut-off controller 104 is used to disable stimulation, stimulation can be re-enabled in one or more of a variety of ways. For example, in some embodiments, stimulation is re-enabled after a predetermined amount of time after it had been disabled. In other examples, the shut-off controller 104 can be used to re-enable stimulation. In some such examples, the patient brings the shut-off controller 104 within a first distance of a sensor (e.g., a magnetic sensor) to disable stimulation, and then removes the shut-off controller 104. Subsequently, once the patient brings the shut-off controller 104 within a second distance of the sensor, stimulation can be re-enabled. In various embodiments, the first distance can be less than the second distance, equal to the second distance, or greater than the second distance. In still further embodiments, another device such as a separate turn-on controller (not shown) or the programmer 100 can be used to re-enable stimulation. Any combination of such re-enabling of stimulation can be used, such as alternatively using either the programmer 100 or the shut-off controller 104 to enable stimulation or combining a minimum "off" time before any other methods can be used to re-enable stimulation.

In some embodiments, rather than entirely disable stimulation, other actions can be taken, such as reducing the magnitude of stimulation. For example, in some embodiments, the shut-off sensor can be used to reduce the signal output by a predetermined amount (e.g., absolute amount, percentage, etc.). In other examples, the shut-off sensor can affect the transfer function of the signal processor to reduce the magnitude of stimulation in a customized way, such as according to frequency or other parameter of an input signal (e.g., from the middle ear sensor).

With reference back to FIG. 1, as described elsewhere herein, the implantable battery and/or communication module can be used to provide power and/or data (e.g., processing instructions) to other system components via lead 190. Different challenges exist for communicating electrical signals through a patient's body. For example, safety standards can limit the amount of current that can safely flow through a patient's body (particularly DC current). Additionally, the patient's body can act as an undesired signal path from component to component (e.g., via contact with the housing or "can" of each component). Various systems and methods can be employed to improve the communication ability between system components.

Figure 10A:
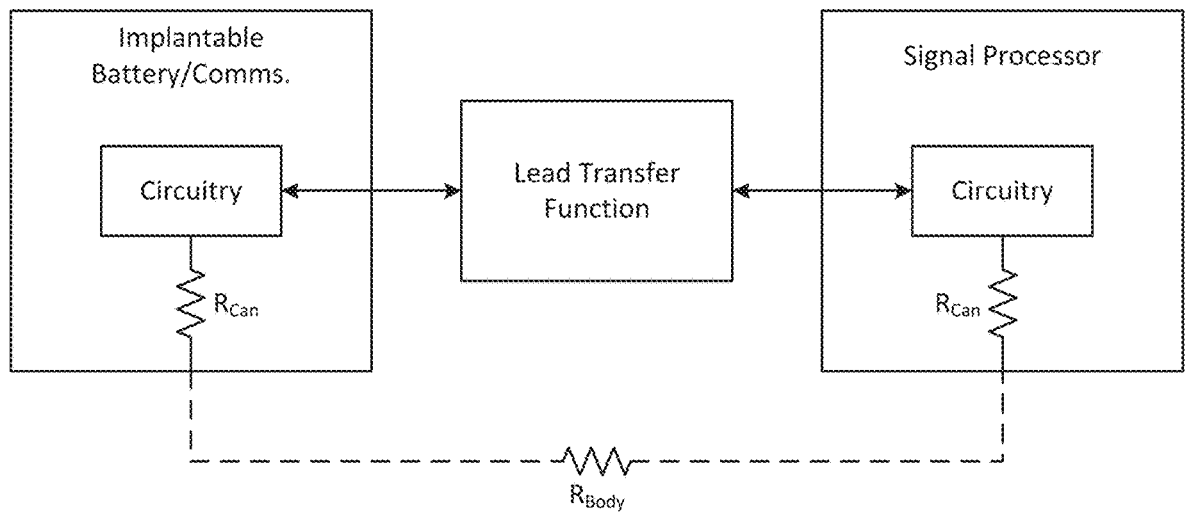
FIG. 10A is a high level electrical schematic showing communication between the implantable battery and/or communication module and the signal processor.

FIG. 10A is a high level electrical schematic showing communication between the implantable battery and/or communication module and the signal processor. In the illustrated embodiment, the implantable battery and/or communication module includes circuitry in communication with circuitry in the signal processor. Communication between the circuitry in the implantable battery and/or communication module and the signal processor can be facilitated by a lead (190), represented by the lead transfer function. The lead transfer function can include, for example, parasitic resistances and capacitances between the leads connecting the implantable battery and/or communication module and the signal processor and the patient's body and/or between two or more conductors that make up the lead (e.g., 191). Signals communicated from the circuitry of the implantable battery and/or communication module to the circuitry in the signal processor can include electrical power provided to operate and/or stimulate system components (e.g., the middle ear sensor, signal processor, electrical and/or acoustic stimulator, and/or cochlear electrode) and/or data (e.g., processing data regarding the transfer function of the signal processor).

As discussed elsewhere herein, the body of the patient provides an electrical path between system components, such as the "can" of the implantable battery and/or communication module and the "can" of the signal processor. This path is represented in FIG. 10A by the flow path through $R_{Body}$. Thus, the patient's body can provide undesirable signal paths which can negatively impact communication between components. To address this, in some embodiments, operating circuitry in each component can be substantially isolated from the component "can" and thus the patient's body. For example, as shown, resistance $R_{Can}$ is positioned between the circuitry and the "can" of both the implantable battery and/or communication module and the signal processor.

While being shown as $R_{Can}$ in each of the implantable battery and/or communication module and the signal processor, it will be appreciated that the actual value of the resistance between the circuitry and respective "can" of different elements is not necessarily equal. Additionally, $R_{Can}$ need not include purely a resistance, but can include other components, such as one or more capacitors, inductors, and the like. That is, $R_{Can}$ can represent an insulating circuit including any variety of components that act to increase the impedance between circuitry within a component and the "can" of the component. Thus, $R_{Can}$ can represent an impedance between the operating circuitry of a component and the respective "can" and the patient's tissue. Isolating the circuitry from the "can" and the patient's body acts to similarly isolate the circuitry from the "can" of other components, allowing each component to operate with reference to a substantially isolated component ground. This can eliminate undesired communication and interference between system components and/or between system components and the patient's body.

Figure 10B:
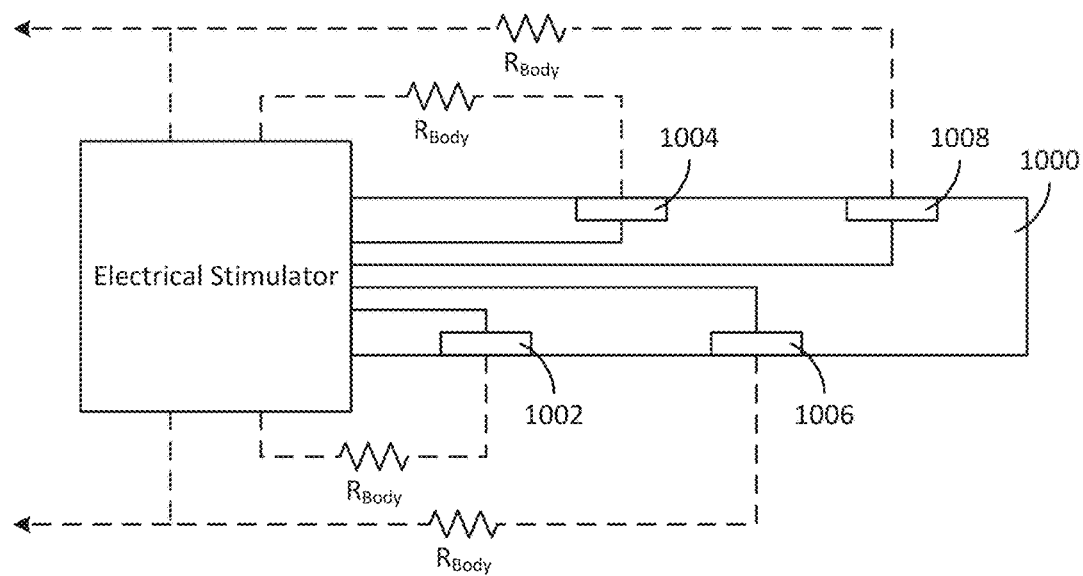
FIG. 10B illustrates an exemplary schematic diagram illustrating a cochlear electrode having a plurality of contact electrodes and fixedly or detachably connected to an electrical stimulator.

For example, as described elsewhere herein, in some examples, an electrical stimulator can provide an electrical stimulus to one or more contact electrodes on a cochlear electrode implanted in a patient's cochlear tissue. FIG. 10B illustrates an exemplary schematic diagram illustrating a cochlear electrode having a plurality of contact electrodes and fixedly or detachably connected to an electrical stimulator. As shown, the cochlear electrode 1000 has four contact electrodes 1002, 1004, 1006, and 1008, though it will be appreciated that any number of contact electrodes is possible. As described elsewhere herein, the electrical stimulator can provide electrical signals to one or more such contact electrodes in response to an output from the signal processor according to the transfer function thereof and a received input signal.

Because each contact electrode 1002-1008 is in contact with the patient's cochlear tissue, each is separated from the "can" of the electrical stimulator (as well as the "cans" of other system components) via the impedance of the patient's tissue, shown as $R_{Body}$. Thus, if the circuitry within various system components did not have sufficiently high impedance (e.g., $R_{Can}$) to the component "can", electrical signals may stimulate undesired regions of the patient's cochlear tissue. For instance, stimulation intended for a particular contact electrode (e.g., 1002) may lead to undesired stimulation of other contact electrodes (e.g., 1004, 1006, 1008), reducing the overall efficacy of the system. Minimizing the conductive paths between system components (e.g., to the contact electrodes of a cochlear electrode) due to the patient's body, such as by incorporating impedances between component circuitry and the corresponding "can" via $R_{Can}$, can therefore improve the ability to apply an electrical stimulus to only a desired portion of the patient's body.

It will be appreciated that the term $R_{Body}$ is used herein to generally represent the resistance and/or impedance of the patient's tissue between various components, and does not refer to a specific value. Moreover, each depiction or $R_{Body}$ in the figures does not necessarily represent the same value of resistance and/or impedance as the others.

Figure 11A:
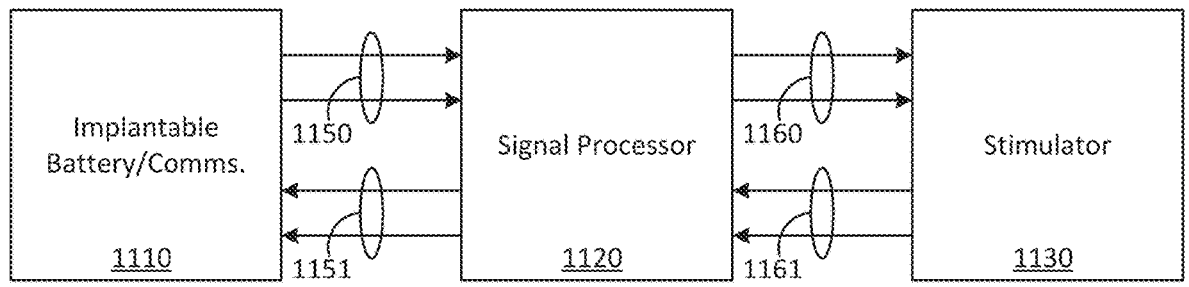
FIG. 11A shows a high level schematic diagram illustrating an exemplary communication configuration between an implantable battery and/or communication module, a signal processor, and a stimulator in an exemplary cochlear implant system.

FIG. 11A shows a high level schematic diagram illustrating an exemplary communication configuration between an implantable battery and/or communication module, a signal processor, and a stimulator. In the example of FIG. 11A, the implantable battery and/or communication module 1110 is in two-way communication with the signal processor 1120. For instance, the implantable battery and/or communication module 1110 can communicate power and/or data signals 1150 to the signal processor 1120. In some examples, the power and data signals 1150 can be included in a single signal generated in the implantable battery and/or communication module 1110 and transmitted to the signal processor 1120. Such signals can include, for example, a digital signal transmitted with a particular clock rate, which in some embodiments, can be adjustable, for example, via the implantable battery and/or communication module 1110.

In some embodiments, the signal processor 1120 can communicate information to the implantable battery and/or communication module 1110 (e.g., via signals 1151), for example, feedback information and/or requests for more power, etc. The implantable battery and/or communication module 1110 can, in response, adjust its output to the signal processor 1120 (e.g., an amplitude, duty cycle, clock rate, etc.) in order to accommodate for the received feedback (e.g., to provide more power, etc.). Thus, in some such examples, the implantable battery and/or communication module 1110 can communicate power and data (e.g., via 1150) to the signal processor 1120, and the signal processor 1120 can communicate various data back to the implantable battery and/or communication module 1110 (e.g., via 1151).

In some embodiments, similar communication can be implemented between the signal processor 1120 and the stimulator 1130, wherein the signal processor 1120 provides power and data to the stimulator 1130 (e.g., via 1160) and receives data in return from the stimulator 1130 (e.g., via 1161). For example, the signal processor 1120 can be configured to output signals (e.g., power and/or data) to the stimulator 1130 (e.g., based on received inputs from a middle ear sensor or other device) via a similar communication protocol as implemented between the implantable battery and/or communication module 1110 and the signal processor 1120. Similarly, in some embodiments, the stimulator can be configured to provide feedback signals to the signal processor, for example, representative of an executed stimulation process. Additionally or alternatively, the stimulator may provide diagnostic information, such as electrode impedance and neural response telemetry or other biomarker signals.

Figure 11B:
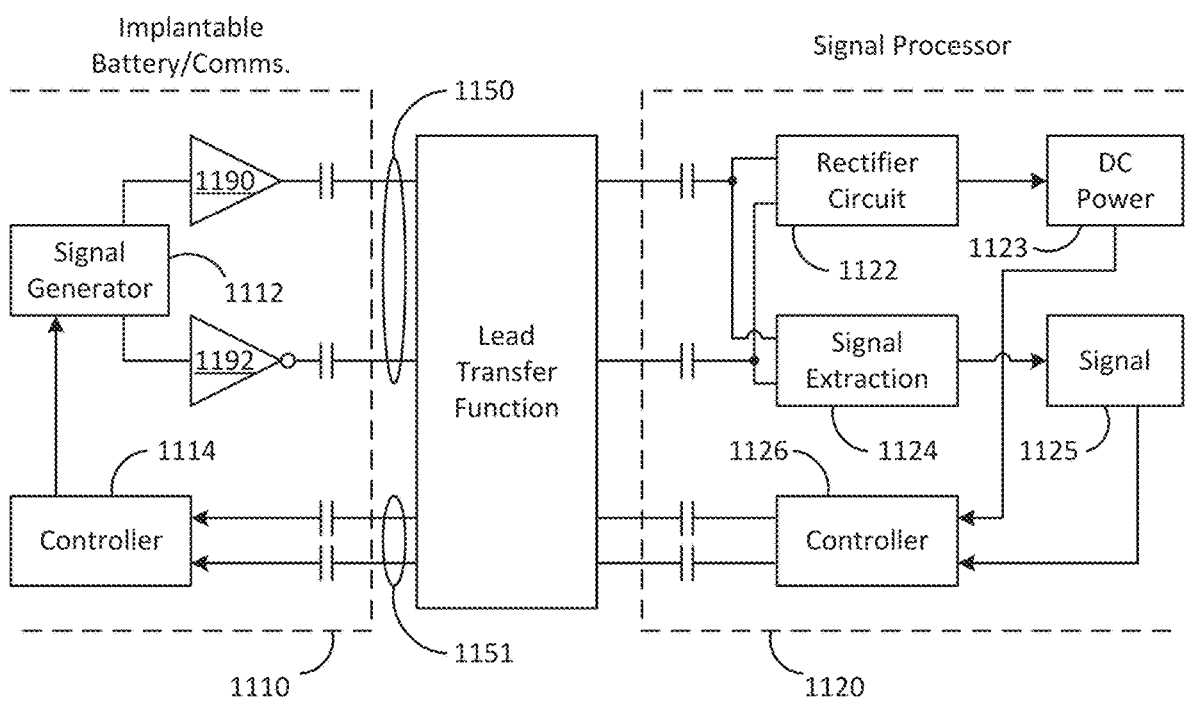
FIG. 11B is a schematic diagram illustrating exemplary electrical communication between an implantable battery and/or communication module and a signal processor in a cochlear implant system according to some embodiments.

FIG. 11B is a schematic diagram illustrating exemplary electrical communication between an implantable battery and/or communication module and a signal processor in a cochlear implant system according to some embodiments. In the illustrated embodiment, the implantable battery and/or communication module 1110 includes a signal generator 1112 configured to output a signal through a lead (e.g., 190) to the signal processor 1120. As described with respect to FIG. 11A, in some examples, the signal generator 1112 is configured to generate both data and power signals (e.g., 1150) for communication to the signal processor 1120. In some embodiments, the signal generator 1112 generates a digital signal for communication to the signal processor 1120. The digital signal from the signal generator 1112 can be communicated to the signal processor 1120 at a particular clock rate. In some examples, the signals are generated at approximately 30 kHz. In various examples, data and power frequencies can range from approximately 100 Hz to approximately 10 MHz, and in some examples, may be adjustable, for example, by a user.

In the illustrated embodiment, the implantable battery and/or communication module 1110 includes a controller in communication with the signal generator 1112. In some examples, the controller is capable of adjusting communication parameters such as the clock rate of the signal generator 1112. In an exemplary embodiment, the controller and/or the signal generator 1112 can communicate with, for example, a patient's external programmer (e.g., as shown in FIG. 1). The controller and/or signal generator 1112 can be configured to communicate data to the signal processor 1120 (e.g., via 1151), such as updated firmware, signal processor 1120 transfer functions, or the like.

As shown, the signal generator 1112 outputs the generated signal to an amplifier 1190 and an inverting amplifier 1192. In some examples, both amplifiers are unity gain amplifiers. In some examples comprising digital signals, the inverting amplifier 1192 can comprise a digital NOT gate. The output from the amplifier 1190 and the inverting amplifier 1192 are generally opposite one another and are directed to the signal processor 1120. In some embodiments, the opposite nature of the signals output to the signal processor 1120 from amplifiers 1190 and 1192 results in a charge-neutral communication between the implantable battery and/or communication module 1110 and the signal processor 1120, such that no net charge flows through the wearer.

In the illustrated example of FIG. 11B, the receiving circuitry in the signal processor 1120 comprises a rectifier circuit 1122 that receives signals (e.g., 1150) from the amplifier 1190 and the inverting amplifier 1192. Since the output of one of the amplifiers 1190 and 1192 will be high, the rectifier circuit 1122 can be configured to receive the opposite signals from the amplifiers 1190 and 1192 and generate therefrom a substantially DC power output 1123. In various embodiments, the DC power 1123 can be used to power a variety of components, such as the signal processor 1120 itself, the middle ear sensor, the electrical and/or acoustic stimulator, or the like. The rectifier circuit 1122 can include any known appropriate circuitry components for rectifying one or more input signals, such as a diode rectification circuit or a transistor circuit, for example.

As described elsewhere herein, the implantable battery and/or communication module 1110 can communicate data to the signal processor 1120. In some embodiments, the controller and/or the signal generator 1112 is configured to encode the data for transmission via the output amplifiers 1190 and 1192. The signal processor 1120 can include a signal extraction module 1124 configured to extract the data signal 1125 from the signal(s) (e.g., 1150) communicated to the signal processor 1120 to produce a signal for use by the signal processor 1120. In some examples, the signal extraction module 1124 is capable of decoding the signal that was encoded by the implantable battery and/or communication module 1110. Additionally or alternatively, the signal extraction module 1124 can extract a signal 1125 resulting from the lead transfer function. In various examples, the extracted signal 1125 can include, for example, an updated transfer function for the signal processor 1120, a desired stimulation command, or other signals that affect operation of the signal processor 1120.

In the illustrated example, the signal processor 1120 includes a controller 1126 that is capable of monitoring the DC power 1123 and the signal 1125 received from the implantable battery and/or communication module 1110. The controller 1126 can be configured to analyze the received DC power 1123 and the signal 1125 and determine whether or not the power and/or signal is sufficient. For example, the controller 1126 may determine that the signal processor 1120 is receiving insufficient DC power for stimulating a cochlear electrode according to the signal processor 1120 transfer function, or that data from the implantable battery and/or communication module 1110 is not communicated at a desired rate. Thus, in some examples, the controller 1126 of the signal processor 1120 can communicate with the controller 1114 of the implantable battery and/or communication module 1110 and provide feedback regarding the received communication. Based on the received feedback from the controller 1126 of the signal processor 1120, the controller 1114 of the implantable battery and/or communication module 1110 can adjust various properties of the signal output by the implantable battery and/or communication module 1110. For example, the controller of the implantable battery and/or communication module 1110 can adjust the clock rate of the communication from the signal generator 1112 to the signal processor 1120.

In some systems, the transmission efficiency between the implantable battery and/or communication module 1110 and the signal processor 1120 is dependent on the clock rate of transmission. Accordingly, in some examples, the implantable battery and/or communication module 1110 begins by transmitting at an optimized clock rate until a change in clock rate is requested via the signal processor 1120, for example, to enhance data transmission (e.g., rate, resolution, etc.). In other instances, if more power is required (e.g., the controller of the signal processor 1120 determines the DC power is insufficient), the clock rate can be adjusted to improve transmission efficiency, and thus the magnitude of the signal received at the signal processor 1120. It will be appreciated that in addition or alternatively to adjusting a clock rate, adjusting an amount of power transmitted to the signal processor 1120 can include adjusting the magnitude of the signal output from the signal generator 1112. In some embodiments, for example, with respect to FIGS. 11A-B, power and data can be communicated, for example, from implantable battery and/or communication module 1110 to the signal processor 1120 at a rate of approximately 30 kHz, and can be adjusted from there as necessary and/or as requested, for example, by the signal processor 1120.

Figure 12A:
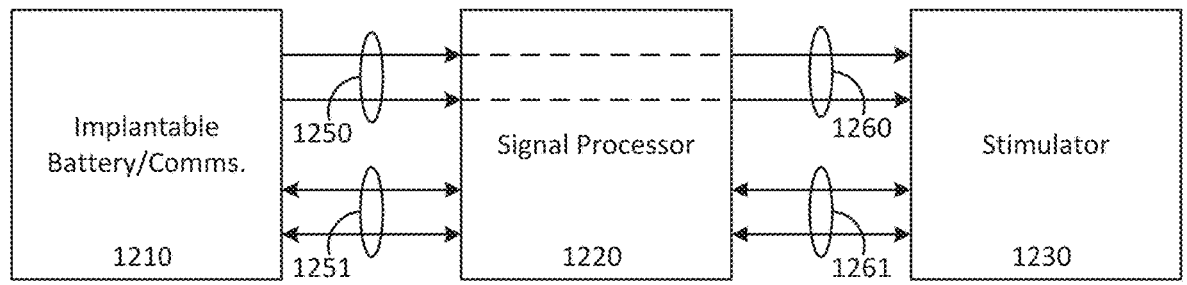
FIG. 12A is an alternative high-level schematic diagram illustrating an exemplary communication configuration between an implantable battery and/or communication module, a signal processor, and a stimulator.

FIG. 12A is an alternative high-level schematic diagram illustrating an exemplary communication configuration between an implantable battery and/or communication module, a signal processor, and a stimulator. In the example of FIG. 12A, the implantable battery and/or communication module 1210 provides signals to the signal processor 1220 via communication link 1250, and is further in two-way communication with the signal processor 1220 via communication link 1251. In the example of FIG. 12A, the implantable battery and/or communication module 1210 can provide power signals to the signal processor 1220 via communication link 1250 and otherwise be in two-way data communication with the signal processor 1220 via communication link 1251. In some such examples, the power and data signals can each include digital signals. However, in some embodiments, the power and data signals are transmitted at different clock rates. In some examples, the clock rate of the data signals is at least one order of magnitude greater than the clock rate of the power signals. For example, in an exemplary embodiment, the power signal is communicated at a clock rate of approximately 30 kHz, while the data communication occurs at a clock rate of approximately 1 MHz. Similarly to the embodiment described in FIG. 11A, in some examples, the clock rate can be adjustable, for example, via the implantable battery and/or communication module 1210.

As described with respect to FIG. 11A, in some embodiments, the signal processor 1220 can communicate information to the implantable battery and/or communication module 1210, for example, feedback information and/or requests for more power, etc. (e.g., via two-way communication 1251). The implantable battery and/or communication module 1210 can, in response, adjust the power and/or data output to the signal processor 1220 (e.g., an amplitude, duty cycle, clock rate, etc.) in order to accommodate for the received feedback (e.g., to provide more power, etc.).

In some embodiments, similar communication can be implemented between the signal processor 1220 and the stimulator 1230, wherein the signal processor 1220 provides power and data to the stimulator 1230 and receives data in return from the stimulator 1230. For example, the signal processor 1220 can be configured to output signals power signals (e.g., via 1260) and data signals (e.g., via 1261) to the stimulator 1230 (e.g., based on received inputs from a middle ear sensor or other device). Such communication can be implemented via a similar communication protocol as implemented between the implantable battery and/or communication module 1210 and the signal processor 1220. In some examples, the power signals provided to the stimulator 1230 (e.g., via 1260) are the same signals received by the signal processor 1220 from the implantable battery and/or communication module 1210 (e.g., via 1250). Additionally, in some embodiments, the stimulator 1230 can be configured to provide feedback signals to the signal processor 1220 (e.g., via 1261), for example, representative of an executed stimulation process.

Figure 12B:
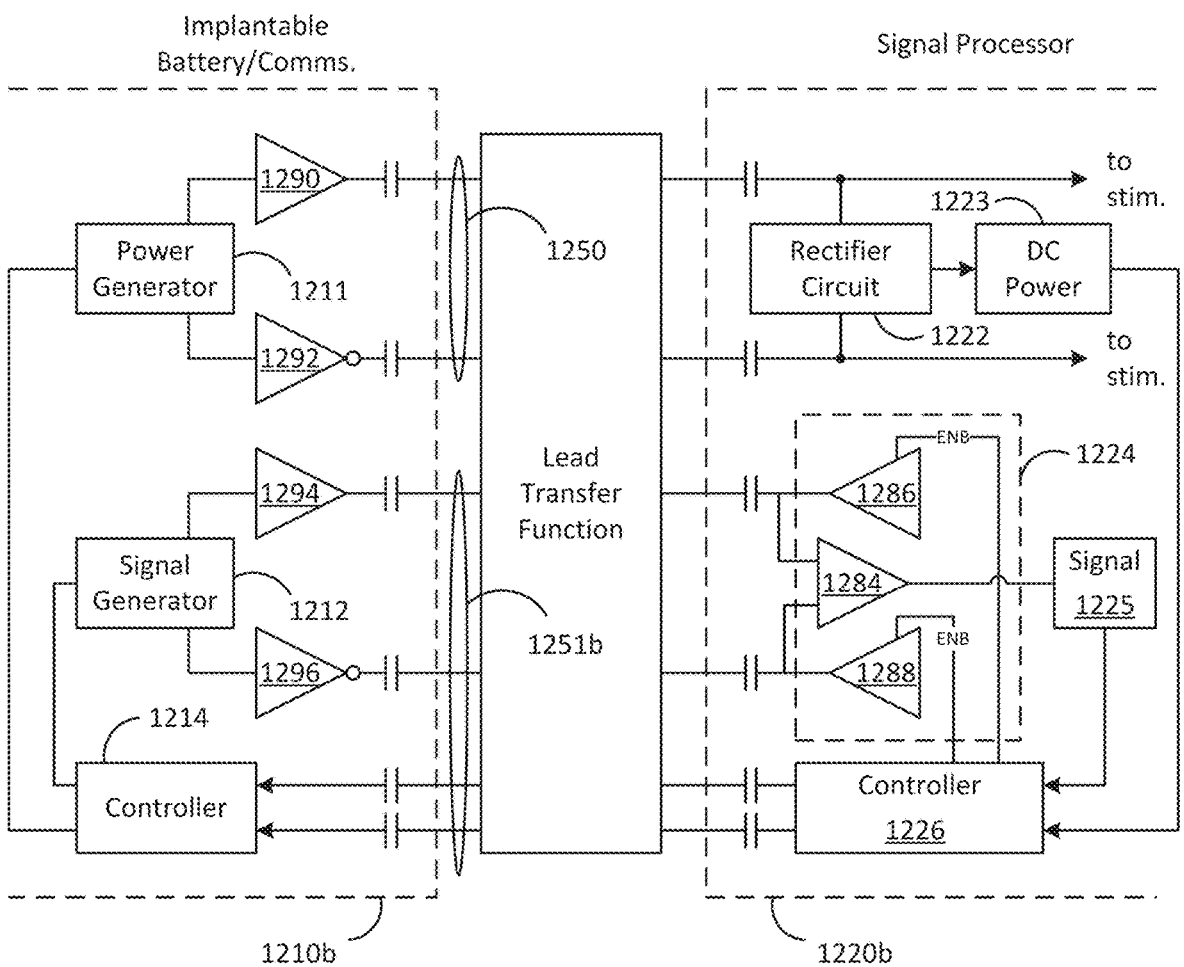
FIG. 12B is an alternative schematic diagram illustrating exemplary electrical communication between an implantable battery and/or communication module and a signal processor in a cochlear implant system similar to that shown in FIG. 12A.

FIG. 12B is an alternative schematic diagram illustrating exemplary electrical communication between an implantable battery and/or communication module 1210b and a signal processor 1220b in a cochlear implant system similar to that shown in FIG. 12A. In the illustrated embodiment of FIG. 12B, the implantable battery and/or communication module 1210b includes a power signal generator 1211 and a separate signal generator 1212. The power signal generator 1211 and signal generator 1212 are each configured to output a signal through a lead (e.g., 190) to the signal processor 1220b. In some embodiments, the power signal generator 1211 and the signal generator 1212 each generates digital signal for communication to the signal processor 1220b. In some such embodiments, the digital signal (e.g., 1250) from the power signal generator 1211 can be communicated to the signal processor 1220b at a power clock rate, while the digital signal (e.g., 1251b) from the signal generator 1212 can be communicated to the signal processor 1220b at a data clock rate that is different from the power clock rate. For instance, in some configurations, power and data can be communicated most effectively and/or efficiently at different clock rates. In an exemplary embodiment, the power clock rate is approximately 30 kHz while the data clock rate is approximately 1 MHz. Utilizing different and separately communicated power and data signals having different clock rates can increase the transfer efficiency of power and/or data from the implantable battery and/or communication module 1210b to the signal processor 1220b.

In the illustrated embodiment, the implantable battery and/or communication module 1210b includes a controller 1214 in communication with the power signal generator 1211 and the signal generator 1212. In some examples, the controller 1214 is capable of adjusting communication parameters such as the clock rate or content of the signal generator 1212 and/or the power signal generator 1211. In an exemplary embodiment, the controller 1214 and/or the signal generator 1212 or power signal generator 1211 can communicate with, for example, a patient's external programmer (e.g., as shown in FIG. 1). The controller 1214 and/or signal generator 1212 can be configured to communicate data to the signal processor 1220b, such as updated firmware, signal processor 1220b transfer functions, or the like. Additionally or alternatively, the controller 1214 can be configured to transmit signals such as audio or other signals streamed or otherwise received from one or more external devices as described elsewhere herein.

As shown, and similar to the example shown in FIG. 11B, the power signal generator 1211 outputs the generated signal to an amplifier 1290 and an inverting amplifier 1292. In some examples, both amplifiers are unity gain amplifiers. In some examples comprising digital signals, the inverting amplifier 1292 can comprise a digital NOT gate. The output from the amplifier 1290 and the inverting amplifier 1292 are generally opposite one another and are directed to the signal processor 1220b. In the illustrated example, the receiving circuitry in the signal processor 1220b comprises a rectifier circuit 1222 that receives signals from the amplifier 1290 and the inverting amplifier 1292. Since the output of one of the amplifiers 1290 and 1292 will be high, the rectifier circuit 1222 can be configured to receive the opposite signals from the amplifiers 1290 and 1292 and generate therefrom a substantially DC power output 1223.

In various embodiments, the DC power 1223 can be used to power a variety of components, such as the signal processor 1220b itself, the middle ear sensor, the electrical and/or acoustic stimulator 1230, or the like. The rectifier circuit 1222 can include any known appropriate circuitry components for rectifying one or more input signals, such as a diode rectification circuit or a transistor circuit, for example. In some embodiments, signals from the power signal generator 1211 are generated at a clock rate that is optimal for transmitting power through the lead (e.g., approximately 30 kHz). In the illustrated example of FIG. 12B, the rectifier circuit 1222 can be arranged in parallel with power lines that are configured to communicate power signals to other components within the system, such as the stimulator 1230, for example. For instance, in some embodiments, the same power signal (e.g., 1250) generated from the power signal generator 1211 and output via amplifiers 1290 and 1292 can be similarly applied to the stimulator 1230. In some such examples, the stimulator 1230 includes a rectifier circuit 1222 similar to the signal processor 1220b for extracting DC power from the power signal and the inverted power signal provided by amplifiers 1290 and 1292, respectively. In alternative embodiments, the signal processor 1220b can similarly provide signals from a separate power signal generator 1211 to provide power signals (e.g., at approximately 30 kHz) to the stimulator 1230 similar to how power is provided from the implantable battery and/or communication module 1210b to the signal processor 1220b in FIG. 12B.

In the example of FIG. 12B, the signal generator 1212 outputs a data signal (e.g., 1251b) to an amplifier 1294 and an inverting amplifier 1296. In some examples, both amplifiers are unity gain amplifiers. In some examples comprising digital signals, the inverting amplifier 1296 can comprise a digital NOT gate. The output from the amplifier 1294 and the inverting amplifier 1296 are generally opposite one another and are directed to the signal processor 1220b.

As described elsewhere herein, in some embodiments, the controller 1214 and/or the signal generator 1212 is configured to encode data for transmission via the output amplifiers 1294 and 1296. The signal processor 1220b can include a signal extraction module 1224 configured to extract the data from the signal(s) 1225 communicated to the signal processor 1220b to produce a signal 1225 for use by the signal processor 1220b. In some examples, the signal extraction module 1224 is capable of decoding the signal that was encoded by the implantable battery and/or communication module 1210b. Additionally or alternatively, the signal extraction module 1224 can extract a resulting signal 1225 resulting from the lead transfer function. In various examples, the extracted signal can include, for example, an updated transfer function for the signal processor 1220b, a desired stimulation command, or other signals that affect operation of the signal processor 1220b.

In the example of FIG. 12B, the signal extraction module 1224 includes a pair of tri-state buffers 1286 and 1288 in communication with signals output from the signal generator 1212. The tri-state buffers 1286 and 1288 are shown as having "enable" (ENB) signals provided by controller 1226 in order to control operation of the tri-state buffers 1286 and 1288 for extracting the signal from the signal generator 1212. Signals from the signal generator 1212 and buffered by tri-state buffers 1286 and 1288 are received by amplifier 1284, which can be configured to produce a signal 1225 representative of the signal generated by the signal generator 1212.

In some examples, communication of signals generated at the signal generator 1212 can be communicated to the signal processor 1220b at a clock rate that is different from the clock rate of the signals generated by the power signal generator 1211. For instance, in some embodiments, power signals from the power signal generator 1211 are transmitted at approximately 30 kHz, which can be an efficient frequency for transmitting power. However, in some examples, the signals from the signal generator 1212 are transmitted at a higher frequency than the signal from the power signal generator 1211, for example, at approximately 1 MHz. Such high frequency data transmission can be useful for faster data transfer than would be available at lower frequencies (e.g., the frequencies for transmitting the signal from the power signal generator 1211). Thus, in some embodiments, power and data can be communicated from the implantable battery and/or communication module 1210b to the signal processor 1220b via different communication channels at different frequencies.

Similar to the embodiment shown in FIG. 11B, in the illustrated example of FIG. 12B, the signal processor 1220b includes a controller 1226 that is in communication with the implantable battery and/or communication module 1210b. In some such embodiments, the controller 1226 in the signal processor 1220b is capable of monitoring the DC power 1223 and/or the signal 1225 received from the implantable battery and/or communication module 1210b. The controller 1126 can be configured to analyze the received DC power 1223 and the signal 1225 and determine whether or not the power and/or signal is sufficient. For example, the controller 1226 may determine that the signal processor 1220b is receiving insufficient DC power for stimulating a cochlear electrode according to the signal processor 1220b transfer function, or that data from the implantable battery and/or communication module 1210b is not communicated at a desired rate. Thus, in some examples, the controller 1226 of the signal processor 1220b can communicate with the controller 1214 of the implantable battery and/or communication module 1210b and provide feedback regarding the received communication. Based on the received feedback from the controller 1226 of the signal processor 1220b, the controller 1214 of the implantable battery and/or communication module 1210b can adjust various properties of the signals output by the power signal generator 1211 and/or the signal generator 1212.

In the illustrated example of FIG. 12B, bidirectional communication 1251b between the implantable battery and/or communication module 1210b and signal processor 1220b comprises signals from the amplifiers 1294 and 1296 in one direction, and communication from controller 1226 to controller 1214 in the other direction. It will be appreciated that a variety of communication protocols and techniques can be used in establishing bidirectional communication 1251b between the implantable battery and/or communication module 1210b and signal processor 1220b.

For example, in some embodiments, the implantable battery and/or communication module 1210b need not include amplifiers 1294 and 1296, and instead transmits a signal and not its inverse to the signal processor 1220b. In other examples, the signal processor includes amplifiers similar to 1294 and 1296, and outputs a signal and its inverse back to the implantable battery and/or communication module 1210b. Additionally or alternatively, in some embodiments, the signal generator 1212 can be integral with the controller 1214 and/or the signal extraction module 1224 can be integral with controller 1226, wherein controllers 1214 and 1226 can be in bidirectional communication via signal generator 1212 and/or the signal extraction module 1224. In general, the implantable battery and/or communication module 1210b and the signal processor 1220b can be in bidirectional communication for communicating data signals separate from the power signals provided by power signal generator 1211.

As described, separate communication channels for power (e.g., 1250) and data (e.g., 1251b) can be used for providing both power and data from the implantable battery and/or communication module 1210b and the signal processor 1220b. This can allow for separate data and power clocking rates in order to improve the power transmission efficiency as well as the data transmission efficiency and/or rate. Moreover, in some examples, if the bidirectional communication (e.g., 1251b) between the implantable battery and/or communication module 1210b and the signal processor 1220b fails (e.g., due to component failure, connection failure, etc.), data for communication from the implantable battery and/or communication module 1210b can be encoded in the power signals from the power signal generator 1211 and transmitted to the signal processor 1220b via 1250. Thus, similar to the embodiment described with respect to FIG. 11B, both power and data can be transmitted via the same signal.

In some examples, the signal extraction module 1224 can be configured to receive data received from the power signal generator 1211, for example, via an actuatable switch that can be actuated upon detected failure of communication 1251b. In other examples, the signal extraction module 1224 and/or the controller 1226 can generally monitor data from the power signal generator 1211 and identify when signals received from the power signal generator 1211 include data signals encoded into the received power signal in order to determine when to consider the power signals to include data.

Accordingly, in some embodiments, the configuration of FIG. 12B can be implemented to establish efficient, bidirectional communication between the implantable battery and/or communication module 1210b and the signal processor 1220b. Failure in bidirectional communication 1251b can be identified manually and/or automatically. Upon detection of failure in the bidirectional communication 1251b, the controller 1214 can encode data into the power signal output from the power signal generator 1211, and power and data can be combined into a single signal such as described with respect to FIG. 11B.

Figure 12C:
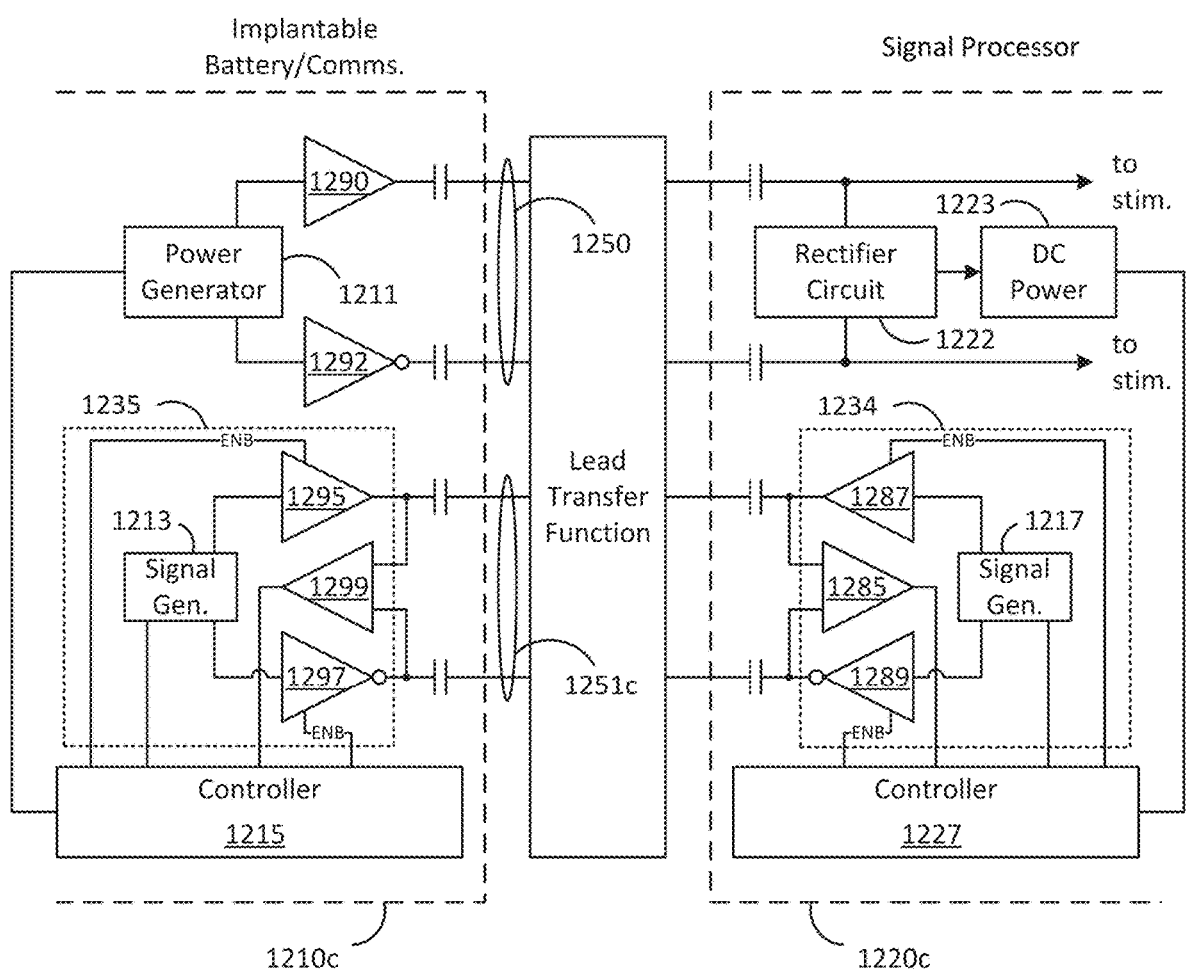
FIG. 12C is another alternative schematic diagram illustrating exemplary electrical communication between an implantable battery and/or communication module and a signal processor in a cochlear implant system similar to that shown in FIG. 12A.

FIG. 12C is another alternative schematic diagram illustrating exemplary electrical communication between an implantable battery and/or communication module 1210c and a signal processor 1220c in a cochlear implant system similar to that shown in FIG. 12A. Similar to the embodiment of FIG. 12B, in the illustrated embodiment of FIG. 12C, the implantable battery and/or communication module 1210c includes a power signal generator 1211 configured to output a signal through a lead (e.g., 190) to the signal processor 1220c. In some embodiments, the power signal generator 1211 generates a digital signal (e.g., 1250) for communication to the signal processor 1220c, for example, at a power clock rate. The power signal generator 1211 and corresponding amplifiers 1290, 1292, as well as rectifier circuit 1222, can operate similar to described with respect to FIG. 12B in order to extract DC power 1223 and, in some examples, output power signals to further system components, such as stimulator 1230.

In the illustrated embodiment, the implantable battery and/or communication module 1210*c* includes a signal generator 1213, which can be capable of providing data signals to the signal processor. In some embodiments, the signal generator 1213 generates a digital signal for communication to the signal processor 1220*c*. In some such embodiments, the digital signal (e.g., 1251*c*) from the signal generator 1213 can be communicated to the signal processor 1220*b* at a data clock rate that is different from the power clock rate. For instance, as described elsewhere herein, in some configurations, power and data can be communicated most effectively and/or efficiently at different clock rates. In an exemplary embodiment, the power clock rate is approximately 30 kHz while the data clock rate is approximately 1 MHz. Utilizing different and separately communicated power and data signals having different clock rates can increase the transfer efficiency of power and/or data from the implantable battery and/or communication module 1210*c* to the signal processor 1220*c*.

The embodiment of FIG. 12C includes a controller 1215 in communication with the power signal generator 1211 and the signal generator 1213. In some examples, the controller 1215 is capable of adjusting communication parameters such as the clock rate or content of the signal generator 1213 and/or the power signal generator 1211. In an exemplary embodiment, the controller 1215 and/or the signal generator 1213 or power signal generator 1211 can communicate with, for example, a patient's external programmer (e.g., as shown in FIG. 1). The controller 1215 and/or signal generator 1213 can be configured to communicate data to the signal processor 1220*c*, such as updated firmware, signal processor 1220*c* transfer functions, or the like.

Similar to the example in FIG. 12B, in the example of FIG. 12C, the signal generator 1213 outputs a data signal (e.g., 1251) to an amplifier 1295 and an inverting amplifier 1297. In some examples, both amplifiers are unity gain amplifiers. In some examples comprising digital signals, the inverting amplifier 1297 can comprise a digital NOT gate. The output from the amplifier 1295 and the inverting amplifier 1297 are generally opposite one another and are directed to the signal processor 1220*c*.

As described elsewhere herein, in some embodiments, the controller 1215 and/or the signal generator 1213 is configured to encode data for transmission via the output amplifiers 1295 and 1297. The signal processor 1220*c* can include a signal extraction module 1234 configured to extract the data from the signal(s) communicated to the signal processor 1220*c* to produce a signal for use by the signal processor 1220*c*. In some examples, the signal extraction module 1234 is capable of decoding the signal that was encoded by the implantable battery and/or communication module 1210*c*. Additionally or alternatively, the signal extraction module 1234 can extract a signal resulting from the lead transfer function. In various examples, the extracted signal can include, for example, an updated transfer function for the signal processor 1220*c*, a desired stimulation command, or other signals that affect operation of the signal processor 1220*c*.

In the example of FIG. 12C, similar to signal extraction module 1224 in FIG. 12B, the signal extraction module 1234 includes a pair of tri-state buffers 1287 and 1289 in communication with signals output from the signal generator 1213. The tri-state buffers 1287 and 1289 are shown as having "enable" (ENB) signals provided by controller 1227 in order to control operation of the tri-state buffers 1287 and 1289 for extracting the signal from the signal generator 1213. Signals from the signal generator 1213 and buffered by tri-state buffers 1287 and 1289 are received by amplifier 1285, which can be configured to produce a signal representative of the signal generated by the signal generator 1213.

As described elsewhere herein, in some examples, communication of signals generated at the signal generator 1213 can be communicated to the signal processor 1220*c* at a clock rate that is different from the clock rate of the signals generated by the power signal generator 1211. For instance, in some embodiments, power signals from the power signal generator 1211 are transmitted at approximately 30 kHz, which can be an efficient frequency for transmitting power. However, in some examples, the signals from the signal generator 1213 are transmitted at a higher frequency than the signal from the power signal generator 1211, for example, at approximately 1 MHz. Such high frequency data transmission can be useful for faster data transfer than would be available at lower frequencies (e.g., the frequencies for transmitting the signal from the power signal generator 1211). Thus, in some embodiments, power and data can be communicated from the implantable battery and/or communication module 1210*c* to the signal processor 1220*c* via different communication channels at different frequencies.

In the illustrated example of FIG. 12C, the signal processor 1220*c* includes a signal generator 1217 and controller 1227 that is in communication with the signal generator 1217. Similar to the operation of signal generator 1213 and amplifiers 1295 and 1299, the signal generator can be configured to produce output signals to amplifiers 1287 and 1289, which can be configured to output signals to the implantable battery and/or communication module 1210*c*.

In some embodiments, the controller 1227 in the signal processor 1220*c* is capable of monitoring the DC power 1223 and/or the signal received from the implantable battery and/or communication module 1210*c*. The controller 1126 can be configured to analyze the received DC power 1223 and the signal and determine whether or not the power and/or signal is sufficient. For example, the controller 1227 may determine that the signal processor 1220*c* is receiving insufficient DC power for stimulating a cochlear electrode according to the signal processor 1220*c* transfer function, or that data from the implantable battery and/or communication module 1210*c* is not communicated at a desired rate. Thus, in some examples, the controller 1227 of the signal processor 1220*c* cause the signal generator 1217 to generate communication signals to send to implantable battery and/or communication module 1210*c*. Such signals can be used to provide feedback regarding signals received by the signal processor 1220*c*, such as the DC power 1223.

In the example of FIG. 12C, amplifiers 1295 and 1297 are shown as including tri-state amplifiers (e.g., tri-state buffers) controllable by the controller 1227. Similar to the configuration in the signal processor 1220*c*, the implantable battery and/or communication module 1210*c* includes a signal extraction module 1235 configured to extract data from the signal(s) communicated to the implantable battery and/or communication module 1210*c* from signal generator 1217 of the signal processor 1220*c*. The signal extraction module 1235 includes tri-state amplifiers 1295 and 1297 in communication with signals output from the signal generator 1217. Signals from the signal generator 1217 and received at tri-state buffers 1295 and 1297 are received by amplifier 1299, which can be configured to produce a signal representative of the signal generated by the signal generator 1217 to controller 1215 of the implantable battery and/or communication module 1210. Thus, in some embodiments, the controller 1227 of the signal processor 1220c is configured to communicate data back to the implantable battery and/or communication module 1210a via amplifiers 1287 and 1289.

As described with respect to other embodiments, based on the received feedback from the controller 1227 of the signal processor 1220c, the controller 1215 of the implantable battery and/or communication module 1210c can adjust various properties of the signals output by the power signal generator 1211 and/or the signal generator 1213.

Thus, in the illustrated example of FIG. 12C, bidirectional communication 1251 between the implantable battery and/or communication module 1210c and signal processor 1220c includes communication between different signal extraction modules 1235 and 1234. As shown, both the implantable battery and/or communication module 1210c and the signal processor 1220c include a controller (1215, 1227) that communicates with a signal generator (1213, 1217) for producing output signals. The signal generator (1213, 1217) outputs signals via tri-state amplifiers, including one inverting amplifier (1297, 1289) for communication across bidirectional communication 1251c for receipt by the other signal extraction module (1234, 1235).

Thus, in some embodiments, bidirectional communication 1251c between the implantable battery and/or communication module 1210c and the signal processor 1220c can be enabled by each of the implantable battery and/or communication module and the signal processor receiving and transmitting data via approximately the same communication structure as the other. In some such examples, the implantable battery and/or communication module 1210c and the signal processor 1220c include data extraction modules 1235 and 1234, respectively, configured both to output signals from a signal generator (e.g., via 1213 or 1217) and receive and extract signals (e.g., via 1299 and 1285).

In the example of FIG. 12C, of tri-state amplifiers 1295 and 1297 that selectively (e.g., via "enable" control from controller 1215) output the signal from signal generator 1213, amplifier 1297 is shown as an inverting amplifier. Similarly, of tri-state amplifiers 1287 and 1289 that selectively (e.g., via "enable" control from controller 1227) output the signal from signal generator 1217, amplifier 1289 is shown as an inverting amplifier. As described elsewhere herein, communicating a signal and its inverse (e.g., via 1295 and 1297) allows communication with no net charge flow between the implantable battery and/or communication module 1210c and the signal processor 1220c. Thus, bidirectional communication between the implantable battery and/or communication module 1210c and the signal processor 1220c can be performed without a net charge flow between the components.

As described elsewhere herein, power from power generator 1211 and data from signal generator 1213 (and/or signal generator 1217) can be communicated at different clocking rates to optimize power and data transfer. In some examples, if data communication (e.g., via bidirectional communication 1251c) fails, the controller 1215 can be configured to control power generator 1211 to provide both power and data signals via amplifiers 1290 and 1292, for example, as described with respect to FIG. 11B.

Accordingly, in some embodiments, the configuration of FIG. 12C can be implemented to establish efficient, bidirectional communication between the implantable battery and/or communication module 1210 and the signal processor 1220. Failure in bidirectional communication 1251 can be identified manually and/or automatically. Upon detection of failure in the bidirectional communication 1251, the controller 1215 can encode data into the power signal output from the power signal generator 1211, and power and data can be combined into a single signal such as described with respect to FIG. 11B.

As discussed elsewhere herein, different safety standards can exist regarding electrical communication within the patient's body. For example, safety standards can limit the amount of current that can safely flow through a patient's body (particularly DC current). As shown in FIGS. 11B, 12B, and 12C, each of the illustrated communication paths between the implantable battery and/or communication module and the signal processor are coupled to output capacitors. The capacitors positioned at the inputs and outputs of the implantable battery and/or communication module and the signal processor can substantially block DC current from flowing therebetween while permitting communication of AC signals.

As described elsewhere herein, in some embodiments, the data communicated between the implantable battery and/or communication module and the signal processor (e.g., from the signal generator) is encoded. In some such examples, the encoding can be performed according to a particular data encoding method, such as an 8$b$/10$b$ encoding scheme, to achieve DC balance in the communicated signal. For example, in some embodiments, data is encoded such that the numbers of high and low bits communicated between components at each clock signal meet certain criteria to prevent a charge of a single polarity from building up on any of the capacitors. Such encoding can minimize the total charge that flows between the implantable battery and/or communication module and the signal processor during communication.

While described and illustrated as representing communication between the implantable battery and/or communication module and the signal processor, it will be appreciated that communication configurations such as shown in FIGS. 10, 11A, 11B, 12A, 12B, and 12C can be implemented between any pair of devices generally in communication with one another. For example, isolating circuitry (e.g., $R_{Can}$) can be included in any of the system components (e.g., middle ear sensor, acoustic stimulator, electrical stimulator, etc.) to effectively isolate the ground signals from each component from its respective can. Similarly, the exemplary capacitive AC coupling with DC blocking capacitors and DC balancing encoding as described elsewhere herein can be incorporated as the communication interface between any two communicating components.

As described, data can be communicated from the implantable battery and/or communication module to the signal processor for a variety of reasons. In some examples, data is that communicated to the implantable battery and/or communication module from an external component, such as a programmer as shown in FIG. 1. In an exemplary process, a programmer, such as a clinician's computer, can be used to communicate with a patient's fully implanted system via a communication configuration such as shown in FIG. 11B, 12B, or 12C. For example, a programmer can communicate wirelessly (e.g., via Bluetooth or other appropriate communication technique) with the patient's implantable battery and/or communication module. Signals from the programmer can be sent from the implantable battery and/or communication module to the signal processor via the communication configurations of FIG. 11B, 12B, or 12C.

During such processes, a clinician can communicate with the signal processor, and, in some cases, with other components via the signal processor. For example, the clinician can cause the signal processor to actuate an electrical and/or an acoustic stimulator in various ways, such as using various electrical stimulation parameters, combinations of active contact electrodes, various acoustic stimulation parameters, and various combinations thereof. Varying the stimulation parameters in real time can allow the clinician and patient to determine effectiveness of different stimulation techniques for the individual patient. Similarly, the clinician can communicate with the signal processor to update transfer function. For example, the clinician can repeatedly update the transfer function signal processor while testing the efficacy of each one on the individual patient. In some examples, combinations of stimulation parameters and signal processor transfer functions can be tested for customized system behavior for the individual patient.

Additional Input Signals/Sources

As described elsewhere herein, while many examples show a middle ear sensor being in communication with an implanted signal processor, in various embodiments, one or more additional or alternative input sources can be included. For instance, in some embodiments, a microphone can be implanted under a user's skin and can be placed in communication with the signal processor (e.g., via a detachable connector such as 171). The signal processor can receive input signals from the implanted microphone and provide signals to the stimulator based on the received input signal and the signal processor transfer function.

Figure 13:
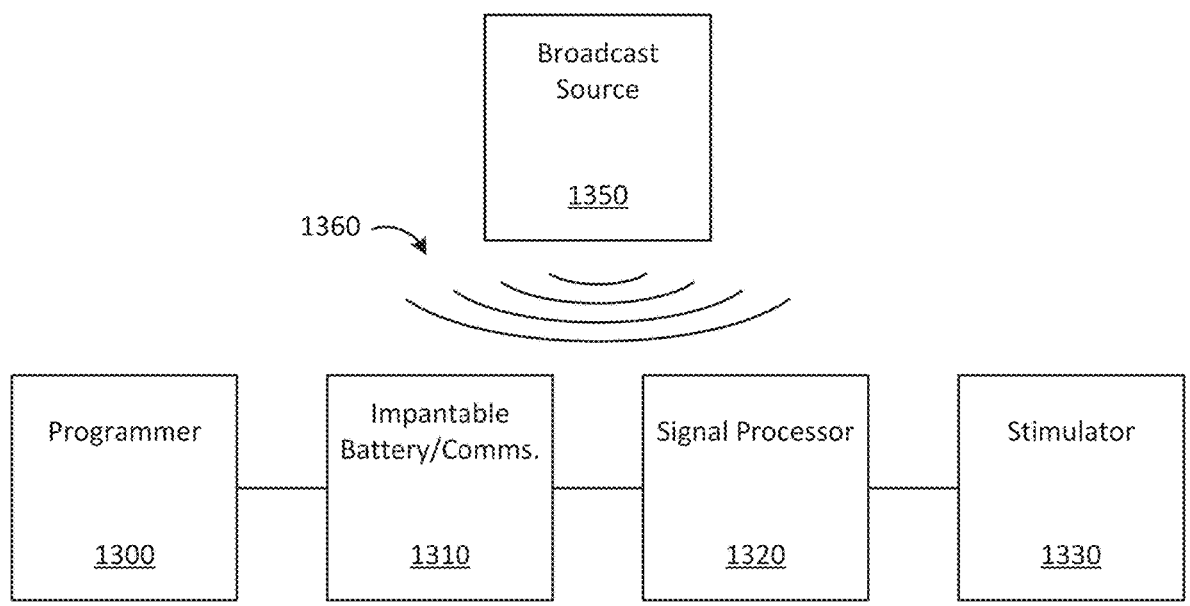
FIG. 13 is a process flow diagram illustrating an exemplary process for establishing a preferred transfer function for a patient.

Additionally or alternatively, one or more system components can be configured to receive broadcast signals for converting into stimulation signals. FIG. 13 is a schematic system diagram showing an implantable system configured to receive broadcast signals from a broadcast device. As shown in the example of FIG. 13, a broadcast source 1350 broadcasts a signal via communication link 1360. The communication link 1360 can include communication via a variety of communication protocols, such as Wi-Fi, Bluetooth, or other known data transmission protocols. Broadcast source 1350 can include any of a variety of components, such as a media source (e.g., television, radio, etc.), communication device (e.g., telephone, smartphone, etc.), a telecoil or other broadcast system (e.g., at a live performance), or any other source of audio signals that can be transmitted to an implanted system or to an external component of an implanted system (e.g., a system programmer, etc.).

An implantable system including a programmer 1300, an implantable battery and/or communication module 1310, a signal processor 1320, and a stimulator 1330 can generally receive the data from the broadcast source 1350 via communication link 1360. In various embodiments, any number of components in the implantable system can include a receiving device, such as a telecoil, configured to receive broadcast signals for eventual conversion into stimulation signals.

For instance, in some embodiments, programmer 1300 can include a telecoil relay configured to receive broadcast telecoil signals from a broadcast source 1350. The programmer can be configured to subsequently communicate a signal representative of the received broadcast signal to the implantable battery and/or communication module 1310 and/or the signal processor 1320, e.g., via a Bluetooth communication. If the communication is received from the programmer 1300 via the implantable battery and/or communication module 1310, the implantable battery and/or communication module 1310 can communicate the signal to the signal processor, for example, as described in any of FIG. 11A, 11B, 12A, or 12C.

In some such embodiments, the signal processor 1320 can be configured to receive such signals from the implantable battery and/or communication module 1310 and output stimulation signals to the stimulator 1330 based on the received signals and the signal processor transfer function. In other examples, the signal processor 1320 can include a telecoil relay or other device capable of receiving broadcast signals from the broadcast source 1350. In some such embodiments, the signal processor 1320 processes the received signals according to the signal processor transfer function and outputs stimulations signals to the stimulator 1330.

In some embodiments, the signal processor 1320 can be in communication with a plurality of input sources, such as, for example, a combination of an implanted microphone, a middle ear sensor, and a broadcast source 1350 (e.g., via the implantable battery and/or communication module 1310). In some such examples, the signal processor can be programmed with a plurality of transfer functions, each according to respective input sources. In such embodiments, the signal processor can identify which one or more input sources are providing input signals and process each such input signal according to the transfer function associated with its corresponding input source.

In some examples, a signal processor 1320 receiving a plurality of input signals from a corresponding plurality of input sources effectively combines the signals when producing a stimulation signal to the stimulator 1330. That is, in some embodiments, input sources are combined to form the stimulation signal from the signal processor 1320. In some such examples, a user may be able to mix the various received input signals in any way desired. For example, a user may choose to blend a variety of different input streams, such as an input from a middle ear sensor or other implanted device, a signal received from an external device (e.g., a telecoil relay, a Bluetooth connection such as to a smartphone, etc.), and the like. In an exemplary configuration, a user may elect to equally blend two input sources such that the stimulation signal is based 50% on a first input source and 50% on a second input source.

Additionally or alternatively, a user may elect to effectively "mute" one or more input sources so that the signal processor 1320 outputs stimulations signals based on input signals received from unmuted sources. Similarly, a user may be able to select a single source from which to process received input signals. For example, in some embodiments, a user may select to have signals received from broadcast source 1350 processed and converted into stimulation signals while having signals received from, for example, a middle ear sensor, disregarded.

In some examples, direct communication with the signal processor can be used to test the efficacy of a given signal processor transfer function and associated stimulation (e.g., acoustic or electrical) parameters. For example, the programmer can be used to disable input signals from a middle ear sensor or other input source and provide a customized signal to the signal processor to simulate a signal from the input source. The signal processor processes the received signal according to its transfer function, and actuates the electrical stimulator and/or the acoustic stimulator accordingly. The processor can be used to test a variety of customized "sounds" to determine the efficacy of the signal processor transfer function for the given patient for each "sound."

Figure 14:
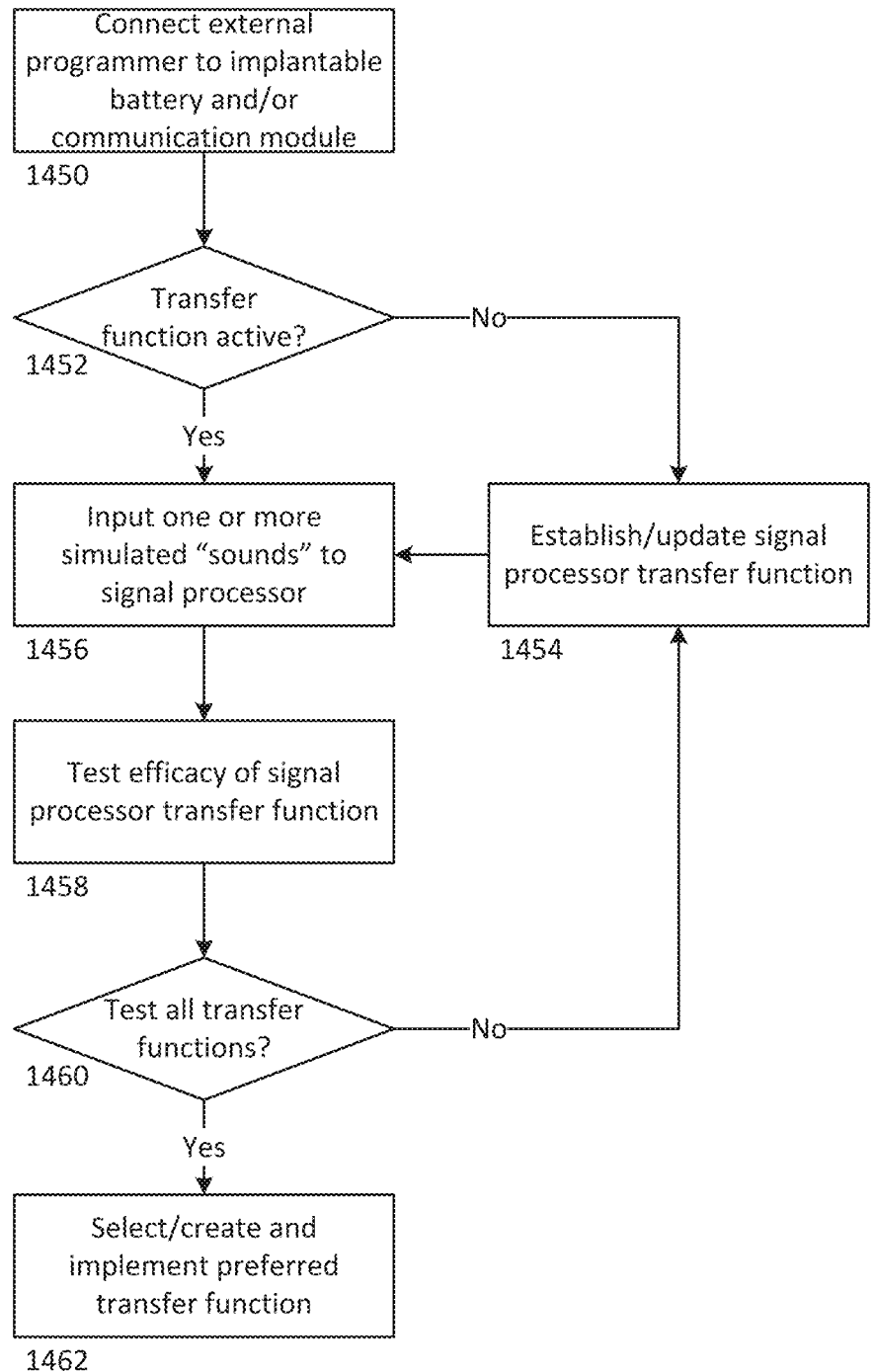
FIG. 14 is a process flow diagram illustrating an exemplary process for establishing a preferred transfer function for a patient.

FIG. 14 is a process flow diagram illustrating an exemplary process for establishing a preferred transfer function for a patient. The method can include connecting an external programmer to the implantable battery and/or communication module (1450). Connecting can include, for example, establishing a wireless connection (e.g., Bluetooth communication) between an external programmer and the implantable battery and/or communication module. The external programmer can include any variety of components capable of providing programming instructions to the implantable battery and/or communication module, such as a computer, smartphone, tablet, or the like.

Once communication is established, if there is no signal processor transfer function active (1452), a signal processor transfer function can be established (1454). If a transfer function is already active, or after one has been established (1454), the programmer can be used to input one or more simulated "sounds" to the signal processor. Such "sounds" can be received and treated by the signal processor as if they were received from an input source such as a middle ear sensor. The "sounds" can be, for example, computer-generated signals designed to simulate various input signals, such as a range of frequencies, phonetic sounds, or other distinguishable sound characteristics.

The process can further include testing the efficacy of the signal processor transfer function (1458). This can include, for example, determining how well the patient responds to each sound provided a given signal processor transfer function. In some examples, this can include rating the transfer function under test for each of the "sounds" and determining an aggregate score for the transfer function based on the score(s) associated with the one or more "sounds."

After testing the efficacy of the signal processor transfer function, if not all desired transfer functions have been tested (1460), the signal transfer function can be updated (1454). The one or more simulated "sounds" can be input to the signal processor (1456) and processed according to the updated transfer function, and the efficacy of the updated transfer function can be tested (1458). Once all desired transfer functions have been tested (1460), a signal processor transfer function for the user can be created or selected and implemented for the patient (1462). In some examples, a best transfer function of the tested transfer functions is selected based on a user preference, a highest score, or other metric. In other examples, composite results from the tested transfer functions can be combined to create a customized transfer function for the patient.

In other examples, rather than continually updating the signal processor transfer function, simulated "sounds" can be pre-processed outside of the signal processor, for example, on site with a clinician or audiologist. For instance, in an exemplary process, one or more simulated sounds can be pre-processed using processing software to establish simulated stimulation signals that would result from a particular input signal being processed via a particular transfer function. In some examples, such signals can be transferred to, for example, the signal processor for directly applying stimulation signals to the wearer.

Communication to the stimulator can be performed, for example, directly from various system components, such as a programmer. In other examples, such communication can be performed via the implantable battery and/or communication module and signal processor. For instance, in an exemplary embodiment, pre-processed signals can be communicated to the implantable battery and/or communication module via a wireless (e.g., Bluetooth) communication. The implantable battery and/or communication module can communicate the pre-processed signals to the signal processor, which can be configured with a unity transfer function. Thus, the signal processor merely passes the pre-processed signals on to the stimulator for performing stimulation.

Figure 15:
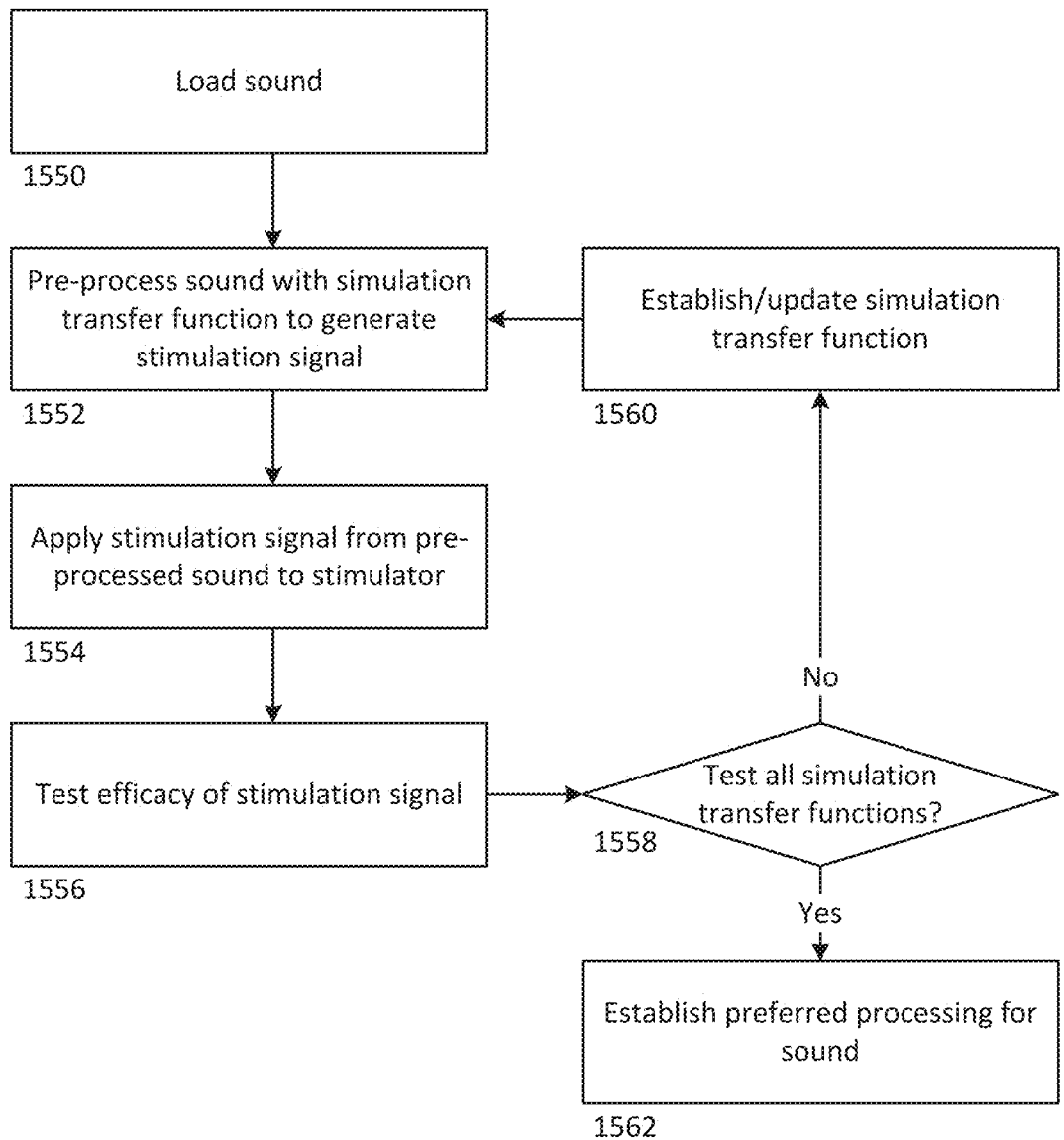
FIG. 15 is a process flow diagram showing an exemplary method of testing the efficacy of one or more sounds using one or more transfer functions via pre-processed signals.

FIG. 15 is a process flow diagram showing an exemplary method of testing the efficacy of one or more sounds using one or more transfer functions via pre-processed signals. In the method of FIG. 15, a sound can be loaded (1550), for example, into an application or processing software capable of processing the received sound. In some examples, the sound can be a simulated sound, such as a computer-generated signal representing a desired sound. In other examples, the sound can include a recording of an actual sound, such as a person's voice or other stimulus. The loaded sound can be pre-processed according to a transfer function to generate a stimulation signal (1552). The pre-processing can be performed, for example, on a stand-alone work station, a system programmer, or the like.

The method of FIG. 15 further comprises the step of applying the stimulation signal from the pre-processed sound to the stimulator of the implanted system (1554). As described elsewhere herein, such communication of the stimulation signal to the stimulator can be performed in a variety of ways, such as directly to the stimulator (e.g., from an external workstation, the user's programmer, etc.) or through the signal processor.

Upon applying the stimulation signal (1554), the method can further include the step of testing the efficacy of the stimulation signal (1556). This can include, for example, testing a user's comprehension of the initial sound from the received stimulation signal, receiving a rating score from the user, or any other appropriate way of resting the efficacy of the stimulation signal. Since the stimulation signal applied in step 1554 is based on the sound and the transfer function used for pre-processing, testing the efficacy of the stimulation signal is similar to testing the efficacy of the transfer function for the given sound.

After testing the efficacy of the stimulation signal, it can be determined whether all simulation transfer functions have been tested for the given sound (1558). If not, the method can include the step of establishing or updating a simulated transfer function (1560), and repeating the steps of pre-processing the sound to establish a stimulation signal (1552), applying the stimulation signal (1554), and testing the efficacy of the stimulation signal (1556) all according to the updated transfer function. Thus, a given sound can be processed according to a plurality of transfer functions, and a plurality of corresponding stimulation signals can be tested with respect to a given user.

In some examples, the process of FIG. 15 can be performed in real time. For instance, in some embodiments, a device in communication with the stimulator in an implanted system (e.g., directly via wireless communication with the stimulator or indirectly via signal processor) can cycle through various simulated transfer functions while pre-processing sound signals prior to communicating them to the user's system. In some such examples, after establishing a preferred processing technique (e.g., simulated transfer function) for a given sound (e.g., in step 1562), the user's signal processor transfer function can be updated to reflect the preferred transfer function for the given sound.

Additionally or alternatively, the process of FIG. 15 can be repeated for a plurality of different sounds. In some embodiments, a plurality of sounds can be pre-processed according to a plurality of different simulated transfer functions, and the resulting generated stimulation signals can be stored in a database. A testing device, such as a workstation, programmer, etc., can be used to carry out the method of FIG. 15 while using the database of stimulations signals to test the efficacy of various transfer functions with respect to various sounds for a user.

In some examples, such a database can be used to fit a user with a particular implant system. For example, stimulation signals generated by pre-processing a plurality of sounds can be communicated to the implanted stimulator of a user having an implanted stimulator and cochlear electrode in order to test the efficacy of the transfer function simulated in the pre-processing. In various examples, a plurality generated stimulation signals associated with a given sound can be applied to the stimulator until a preferred simulated transfer function is established. In other examples, generated stimulation signals representative of a plurality of sounds can be established for each of a plurality of transfer functions, such that each transfer function can be tested on a user for a plurality of sounds prior to testing another transfer function.

FIG. 16 is a schematic representation of an exemplary database of pre-processed sound signals. As shown, the database is represented as a table having n rows corresponding to different sounds (sound 1, sound 2, . . . , sound n) and m columns corresponding to different simulated transfer functions (simulated transfer function 1, simulated transfer function 2, . . . , simulated transfer function m). As shown, at the intersection of each row (i) and each column (j), pre-processing a sound i with a simulated transfer function j results in stimulation signal (i,j). In some embodiments, a table such of stimulation signals generated from pre-processed sounds such as shown in FIG. 16 can be stored in a database of pre-processed sound signals for device fitting for a user.

As described elsewhere herein, in various fitting processes, a sound may be selected from database (e.g., sound 1), and a plurality of different stimulation signals (e.g., stimulation signal (1,1), stimulation signal (1,2), . . . , stimulation signal (1,$m$)) can be communicated to an implanted stimulator. Such stimulation signals generally correspond to the result of the sound (e.g., sound 1) being pre-processed according to various simulated transfer functions (1-$m$). As described with respect to FIG. 15, a preferred stimulation signal (and thus, a preferred corresponding simulated transfer function) can be established for the given sound (e.g., sound 1). A similar process can be repeated for each sound in the database. In various examples, one or more signal processor transfer functions can be communicated to the signal processor based on the determined preferred simulated transfer function(s). For instance, in some example, the simulated transfer function that was preferred among the most sounds may be implemented as the signal processor transfer function. In other embodiments, the signal processor include a plurality of transfer functions, and can apply different transfer functions to different detected sounds depending on the preferred transfer function for each sound.

In other exemplary fitting processes, a plurality of stimulation signals (e.g., stimulation signal (1,1), stimulation signal (2,1), . . . , stimulation signal (n,1)) corresponding to a single simulated transfer function (e.g., simulated transfer function 1) can be applied to a stimulator. Such stimulation signals correspond to a plurality of sounds that are pre-processed according to the single simulated transfer function. This can be used to test the efficacy of the selected transfer function. The process can be repeated for a plurality of simulated transfer functions (e.g., 2-$m$) in order to determine a best transfer function across a variety of sounds (e.g., sounds 1-$n$).

In general, a database of stimulation signals generated by pre-processing sound signals via various transfer functions such as shown in FIG. 16 can be useful for expediting the testing of such transfer functions for a particular user. Pre-processing such sounds allows for the processing to be done, for example, in a lab or on a workstation prior to any fitting process, and allows for efficient application of stimulation signals corresponding to different transfer functions to a user's stimulator without requiring updates of the signal processor. Additionally, such pre-processing can allow for more advanced or computationally demanding processing techniques to be tested for efficacy even if such processing techniques may not yet be effectively implemented by an implanted signal processor (e.g., due to various hardware limitations). Testing the efficacy of such processing techniques can motivate evolution of processing methodologies and hardware capability, for example, in an effort to employ more complex processing techniques in the future.

Various features and functions of implantable systems have been described herein. As described, in various embodiments, system operation(s) can be adjusted based on communication with the implanted system from components located outside of the body while the system remains implanted. In some embodiments, the system may include any number of external components capable of interfacing with the system in a variety of ways.

Figure 17:
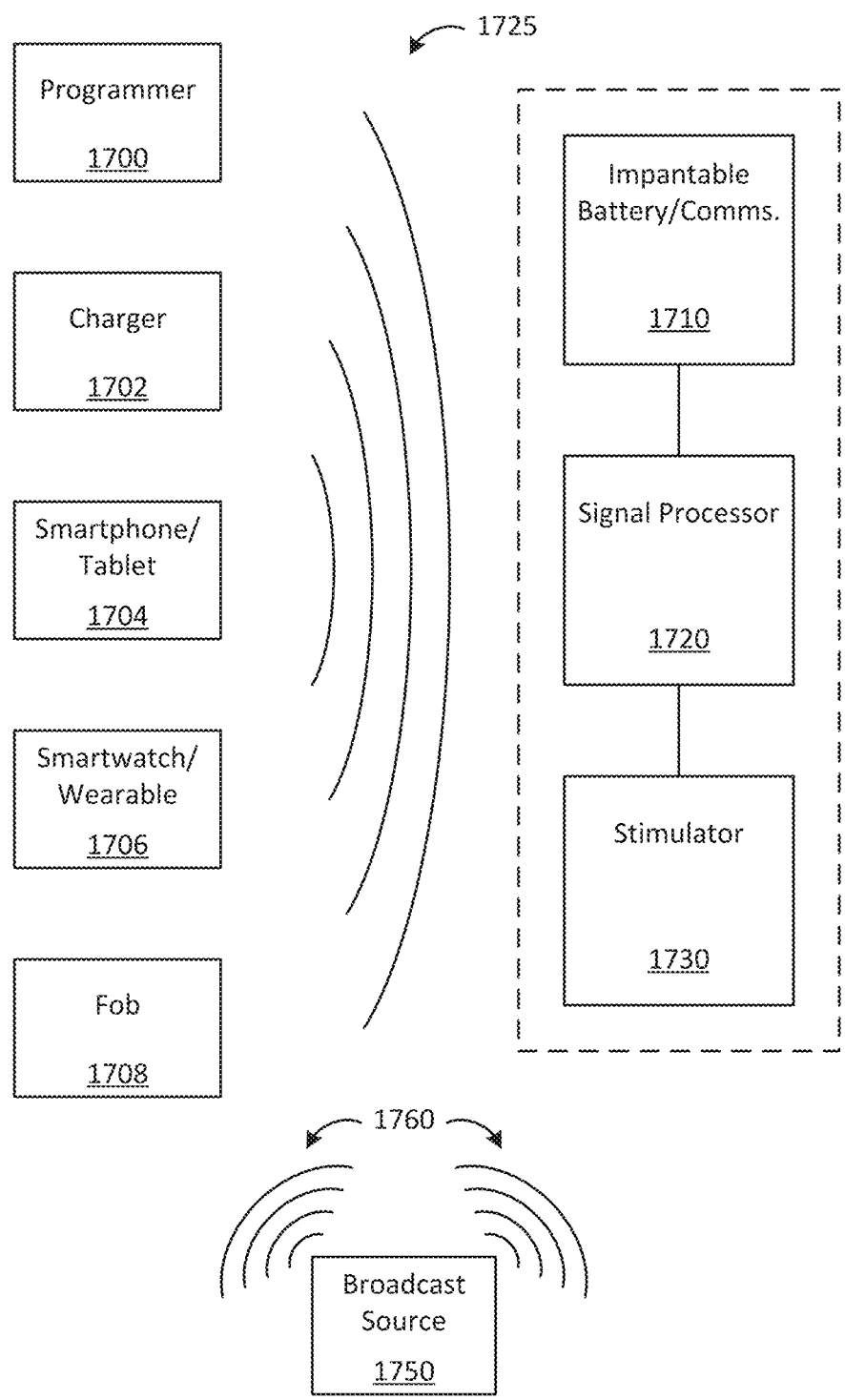
FIG. 17 is a schematic diagram illustrating possible communication between a variety of system components according to some embodiments of a fully-implantable system.
Figure 5:
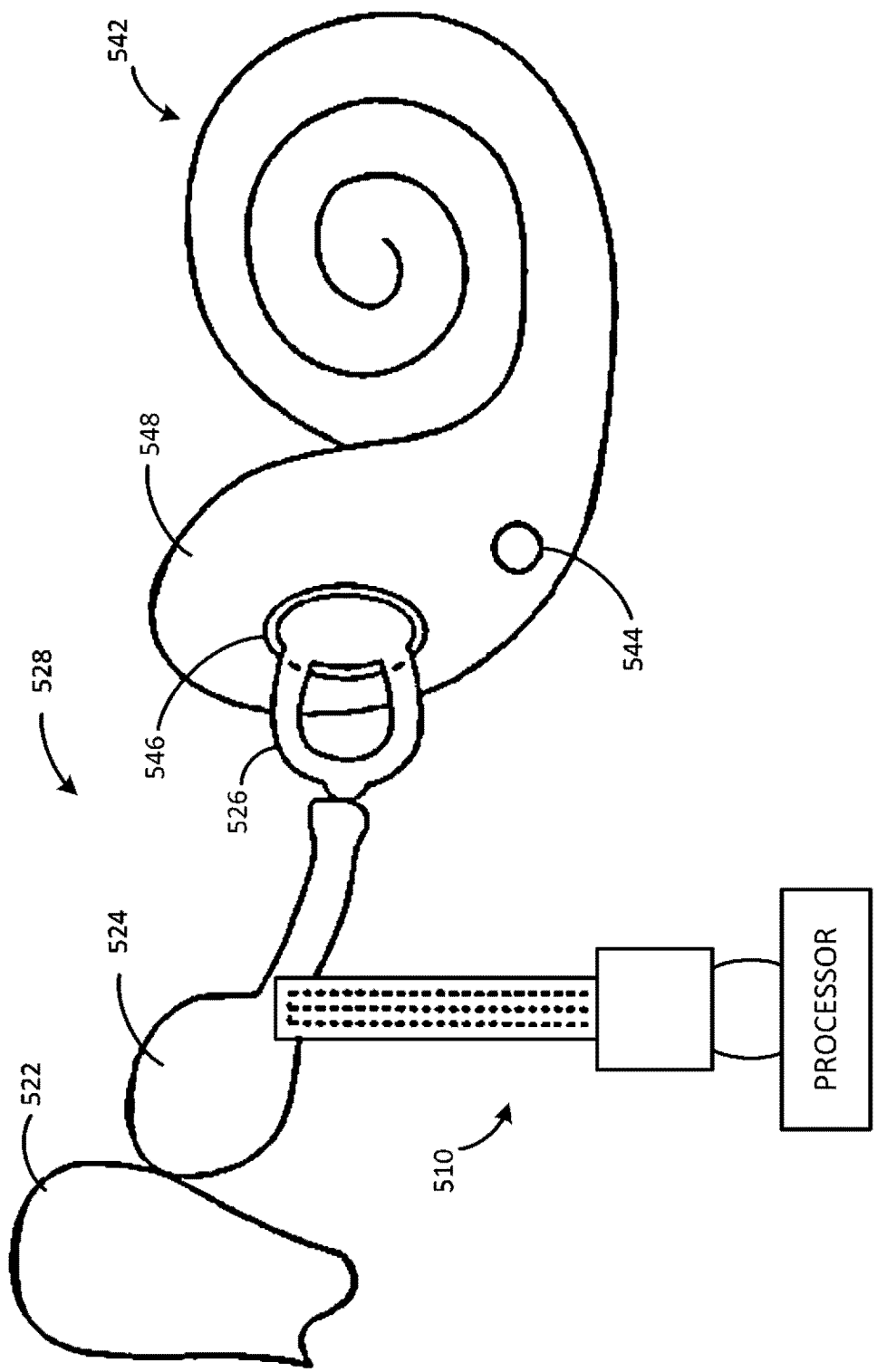
Figure 9:
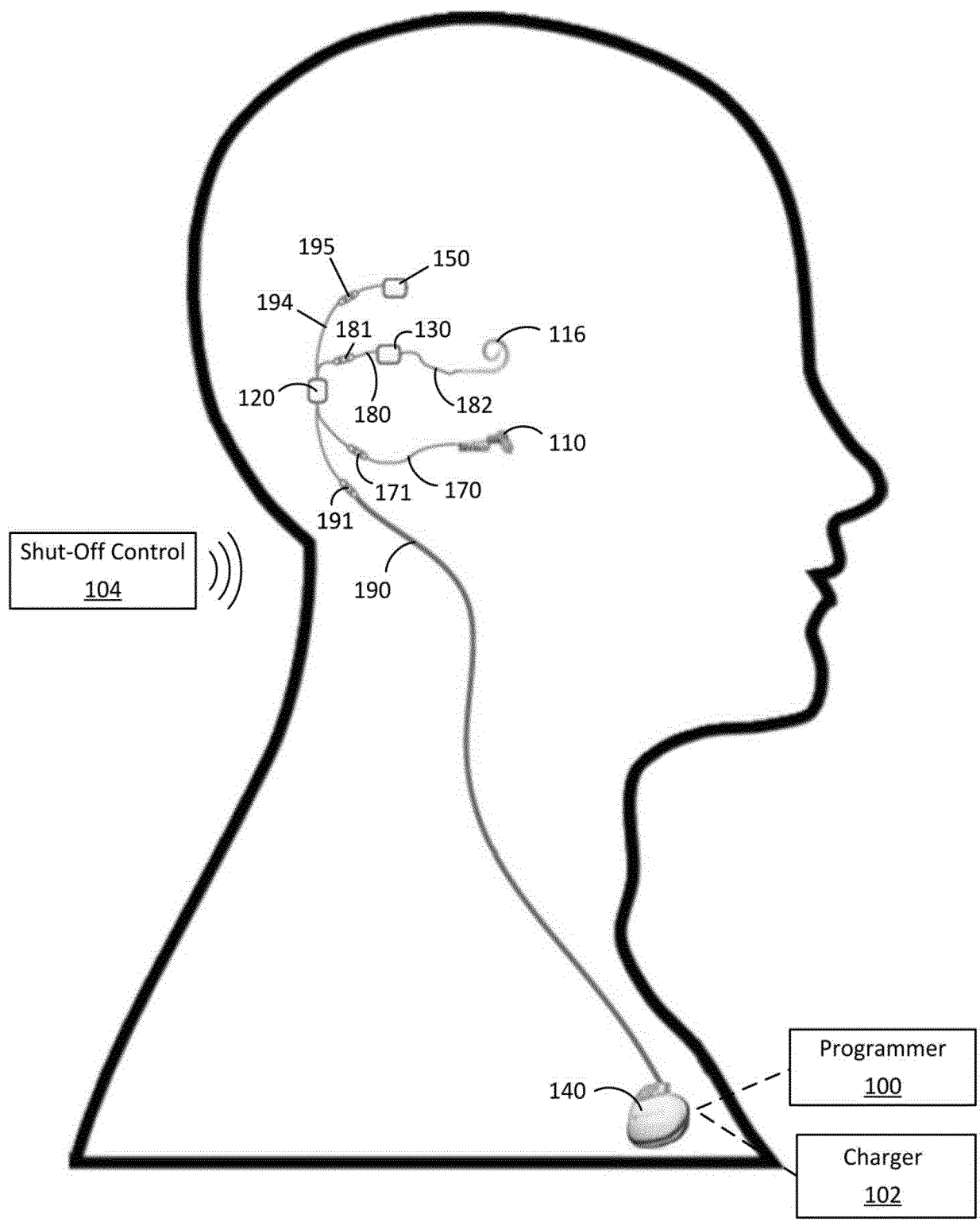

FIG. 17 is a schematic diagram illustrating possible communication between a variety of system components according to some embodiments of a fully-implantable system. In the illustrated embodiment, implanted components (outlined in broken line) of a system include an implantable battery and/or communication module 1710, a signal processor 1720, and a stimulator 1730. Such implanted components can operate according to various examples as described herein in order to effectively stimulate a user (e.g., via electrical and/or acoustic stimulation) in response to received input signals.

The schematic illustration of FIG. 17 includes a plurality of external devices capable of wirelessly interfacing with one or more of the implanted components, for example, via communication link 1725. Such devices can include a programmer 1700, a charger 1702, a smartphone/tablet 1704, a smartwatch or other wearable technology 1706, and a fob 1708. In some examples, such components can communicate with one or more implantable components via one or more communication protocols via wireless communication link 1725, such as Bluetooth, Zigbee, or other appropriate protocols. In various embodiments, different external devices are capable of performing one or more functions associated with system operation. In some such embodiments, each external device is capable of performing the same functions as the others. In other examples, some external devices are capable of performing more functions than others.

For example, a programmer 1700 can be capable of interfacing wirelessly with one or more implantable components in order to control a variety of operating parameters of the implanted system. For example, in some embodiments, programmer 1700 can be configured to adjust a signal processor transfer function or select an operating profile (e.g., associated with a particular signal processor transfer function according to a particular user, environment, etc.). In some examples, the programmer 1700 can be used to establish user profiles, such as preferred signal processor transfer functions, as described elsewhere herein. The programmer 1700 can additionally or alternatively be used to turn the system on or off, adjust the volume of the system, receive and stream input data to the system (e.g., the implantable battery and/or communication module 1710). In some embodiments, the programmer 1700 includes a display for displaying various information to the user. For example, the display can be used to indicate a mode of operation (e.g., a loaded user profile), a remaining power level, or the like. In some such embodiments, the display can function as a user interface by which a user can adjust one or more parameters, such as volume, profile, input source, input mix, and the like.

In some embodiments, a charger 1702 can be used to charge one or more internal batteries or other power supplies within the system, such as in the implantable battery and/or communication module 1710. In some examples, the charger 1702 can include the same functionality as the programmer 1700, including, for instance, a display and/or user interface. In some such embodiments, the programmer 1700 and the charger 1702 can be integrated into a single device.

In some embodiments, various external devices such as a smartphone or tablet 1704 can include an application ("app") that can be used to interface with the implanted system. For example, in some embodiments, a user may communicate (e.g., via link 1725) with the system via the smartphone or tablet 1704 in order to adjust certain operating factors of the system using a predefined app to provide an interface (e.g., a visual interface via a display integrated into the external device). The app can assist the user in adjusting various parameters, such as volume, operating profile, on/off, or the like. In some examples, the smartphone/tablet 1704 can be used to stream input signals to the implanted system, such as media or communication playing on the smartphone/tablet 1704.

In some systems, a smartwatch or other wearable technology 1706 can interact with the system in a similar way as the smartphone/tablet 1704. For example, the smartwatch or other wearable technology 1706 can include an app similar to that operable on the smartphone/tablet to control operation of various aspects of the implanted system, such as volume control, on/off control, etc.

In some embodiments, the fob 1708 can be used to perform basic function with respect to the implanted system. For instance, in some embodiments, a fob 1708 can be used to load/implement a particular operating profile associated with the fob 1708. Additionally or alternatively, the fob 1708 can function similar to the shut-off control 104 of FIG. 1, and can be used to quickly disable and/or mute the system. As described elsewhere herein, in some examples, the same device used to disable and/or mute the system (e.g., fob 1708) can be used to enable and/or unmute the system.

The schematic diagram of FIG. 17 further includes a broadcast source 1750 configured to broadcast signals 1760 that are receivable via one or more external devices and/or one or more implanted system components. Similar to the broadcast source 1350 in FIG. 13, broadcast source 1750 can be configured to emit signals that can be turned into stimulation signals for application by stimulator 1730. Broadcast signals 1760 can include, for example, telecoil signals, Bluetooth signals, or the like. In various embodiments, one or more external devices, such as a programmer 1700, charger 1702, smartphone/tablet 1704, smartwatch/wearable device 1706, and/or fob 1708 can include a component (e.g., a telecoil relay) capable of receiving broadcast signal 1760. The external device(s) can be further configured to communicate a signal to one or more implanted components representative of the received broadcast signal 1760 for applying stimulation to the patient based on the broadcast signal 1760.

Additionally or alternatively, in some embodiments, one or more implanted system components, such as an implantable battery and/or communication module 1710, a signal processor 1720, and/or a stimulator 1730 can be configured to receive broadcast signals 1750. Such component(s) can be used to generate stimulation signals for applying to a user via stimulator 1730 according to the received broadcast signals 1750.

As described, in various embodiments, different external devices can interface with implanted components to adjust operation of the system in various ways. In some embodiments, not all components are capable of performing the same functions as other components. FIG. 18 is a chart showing the various parameters that are adjustable by each of a variety of external devices according to some exemplary systems. In the example of FIG. 18, entries in the chart including an 'X' represent a component configured to perform a corresponding function. Other examples are possible in which different components include different functionality than is represented by the example of FIG. 18.

Generally, the modularity of such systems allows system modifications, such as repairing, replacing, upgrading, etc., of system components and/or transitioning from a partially- to fully-implantable system, to be performed with minimal disturbance of implanted system components. For example, an implanted cochlear electrode and electrical stimulator and/or acoustic stimulator can remain in place while other system components are implanted and/or replaced, reducing the risk of additional procedures damaging the patient's cochlear tissue. Additionally, the communication techniques as described herein can be used to help customize and/or optimize a signal processor transfer function for a particular patient, as well as enable the system to meet safety standards, provide adequate power and data transfer rates between system components, and operate at a high efficiency. It will be appreciated that, while generally described herein with respect to implantable hearing systems, communication techniques described can be used in a variety of other implantable systems, such as various neuromodulation devices/systems, including, for example, pain management, spinal cord stimulation, brain stimulation (e.g., deep brain stimulation), and the like.

Various non-limiting embodiments have been described. These and others are within the scope of the following claims.

The invention claimed is:
1. A modular cochlear implant system comprising:
a cochlear electrode;
a stimulator in electrical communication with the cochlear electrode;
a signal processor in communication with the stimulator;
an input source in communication with the signal processor; and
a first detachable connector configured to detachably connect the signal processor and the input source and to provide communication between the signal processor and the input source when attached; wherein
the signal processor is configured to receive an input signal from the input source and output a stimulation signal to the stimulator based on the received input signal and a transfer function of the signal processor;
the stimulator provides an electrical stimulus to the cochlear electrode based on the stimulation signal; and the cochlear electrode, the stimulator, the signal processor, and the input source are fully implantable into a patient.

2. The implant system of claim 1, further comprising a second detachable connector configured to detachably connect the signal processor and the stimulator and to provide communication between the signal processor and the stimulator when attached.

3. The implant system of claim 1, wherein the input source comprises a middle ear sensor and/or an implantable microphone.

4. The implant system of claim 3, wherein the middle ear sensor is configured to interface with anatomical features of the patient such that input signals generated by the middle ear sensor are based on vibration sensed by the middle ear sensor.

5. The implant system of claim 3, wherein the input source further comprises a wireless receiving device configured to receive a transmitted signal from a source external to the patient.

6. The implant system of claim 5, wherein the signal processor is configured to:
receive a first input signal from the middle ear sensor and/or implantable microphone;
receive a second input signal from the wireless receiving device; and
output a stimulation signal to the stimulator based on the received first input signal, the received second input signal, the transfer function, and a programmable mixing ratio representative of the relative contributions of the first input signal and the second input signal to the output stimulation signal.

7. The implant system of claim 5, further comprising an external programmer in wireless communication with the wireless receiving device, and wherein the external programmer is configured to receive a broadcast signal from a broadcast source and to transmit a transmission signal to the wireless receiving device representative of the broadcast signal received from the broadcast source.

8. The implant system of claim 5, wherein the wireless receiving device comprises a first communication coil, and wherein the source external to the patient comprises a microphone and a second communication coil.

9. The implant system of claim 1, further comprising an implantable battery and a third detachable connector configured to detachably connect the signal processor and the implantable battery such that the implantable battery is configured to provide electrical power to the signal processor via the third detachable connector when the third detachable connector is attached.

10. The implant system of claim 9, wherein the implantable battery further is configured to communicate with an external programming device and to transmit a signal to the signal processor via the third detachable connector representative of information received from the external programming device.

11. The implant system of claim 1, further comprising an acoustic stimulator configured to interface with the patient's ossicular chain, the acoustic stimulator being in electrical communication with the signal processor via a fourth detachable connector.

12. A method of implanting and operating a cochlear implant comprising:
implanting a stimulator and cochlear electrode into a patient such that the cochlear electrode is implanted into the patient's cochlear tissue, the cochlear electrode being electrically coupled to the stimulator;
implanting a signal processor into the patient in communication with the stimulator;
implanting an input source into the patient; and
connecting the signal processor to the input source via a first detachable connector; wherein
the signal processor is programmed with a transfer function to receive an input signal via the input source and output a stimulation signal to the stimulator based on the received input signal and the signal processor transfer function.

13. The method of claim 12, further comprising the steps of:
implanting a power and data communication device into the patient; and
connecting the power and data communication device to the signal processor via a second detachable connector.

14. The method of claim 13, wherein the power and data communication device comprises a coil.

15. The method of claim 12, wherein:
the input source comprises a middle ear sensor.

16. The method of claim 12, further comprising:
implanting a power source into the patient, wherein implanting the power source comprises implanting the power source in the patient's pectoral region; and
connecting the power source to the signal processor via a second detachable connector.

17. A modular cochlear implant system comprising:
a stimulator configured to provide stimulation signals;
an input source configured to receive an input representative of ambient sound and generate an input signal representative of the received input;
a signal processor in communication with the stimulator and the input source, the signal processor being programmed with a transfer function such that the signal processor outputs a stimulation signal to the stimulator based on the input signal received from the input source and the transfer function; wherein
the signal processor is in communication with the input source via a first detachable connector.

18. The implant system of claim 17, further comprising an implantable battery and/or communication module in communication with the signal processor via a second detachable connector and configured to provide electrical power to the signal processor via the second detachable connector.

19. The implant system of claim 17, wherein the stimulator comprises an electrical stimulator in communication with a cochlear electrode, the cochlear electrode including a plurality of contact electrodes; wherein
the stimulation signal from the signal processor comprises a plurality of stimulation signals corresponding to electrical stimulations to be applied at the plurality of contact electrodes according to the received input signal and the transfer function.

20. A method for updating an implanted cochlear implant system in a patient, the cochlear implant system comprising an implanted stimulator, a cochlear electrode implanted into the patient's cochlear tissue and in electrical communication with the implanted stimulator, an implanted first signal processor in communication with the implanted stimulator, and an implanted first input source in communication with the first signal processor via a first detachable connector the method comprising:
disconnecting the implanted first signal processor from the implanted first input source by disconnecting the first detachable connector; and:
(a) removing the implanted first input source and implanting a second input source; and/or (b) removing the implanted first signal processor and implanting a second signal processor; wherein the cochlear electrode remains implanted in the patient during the disconnecting, removing, and implanting steps.

21. The method of claim 20, comprising the step of (a) removing the implanted first input source and implanting a second input source; and wherein the first input source comprises a communication coil and wherein the second input source and the second input source comprises a middle ear sensor; and further comprising the steps of:

connecting the middle ear sensor to either the implanted first or second signal processor via the first detachable connector;

implanting a power source; and connecting the power source to the implanted first or second signal processor via a second detachable connector.

22. The method of claim 20, comprising the step of (b) removing the implanted first signal processor and implanting a second signal processor; and further comprising the step of:

prior to removing the implanted first signal processor, disconnecting the implanted first signal processor from the implanted stimulator by disconnecting a third detachable connector;

connecting the second signal processor to the implanted stimulator via the third detachable connector; and connecting the second signal processor to the implanted first or second input source via the first detachable connector.

* * * * *

UNITED STATES PATENT AND TRADEMARK OFFICE
CERTIFICATE OF CORRECTION

PATENT NO. : 10,646,709 B2  
APPLICATION NO. : 15/679755  
DATED : May 12, 2020  
INVENTOR(S) : Mazanec et al.

Page 1 of 3

It is certified that error appears in the above-identified patent and that said Letters Patent is hereby corrected as shown below:

On the Title Page

Item (72) Inventors: "Paul R. Mazanec, Ham Lake, MN (US); Benjamin R. Whittington, Maplewood, MN (US); Timothy J. Earnest, Vadnais Heights, MN (US)" should read --"Paul R. Mazanec, Ham Lake, MN (US); Benjamin R. Whittington, Maplewood, MN (US); Timothy J. Earnest, Vadnais Heights, MN (US); Joshua J. Wibben, New Brighton, MN (US)"--.

In the Drawings

Sheet 5, Fig. 5, reference numbers 520, 532, 534, 536, and 538, which are not used in the specification, are removed as shown on attached replacement drawing.

Sheet 9, Fig. 9, reference number 110 was used twice. The instance of reference number 110 referring to the implantable battery and/or communication module is replaced with reference number 140 for consistency with the disclosure as shown on attached replacement drawing.

Sheet 9, Fig. 9, reference number 140 was incorrectly applied to the electrical stimulator. This instance of reference number 140 is replaced with reference number 130 for consistency with the disclosure as shown on attached replacement drawing.

Signed and Sealed this  
Twenty-first Day of September, 2021

Drew Hirshfeld  
*Performing the Functions and Duties of the*  
*Under Secretary of Commerce for Intellectual Property and*  
*Director of the United States Patent and Trademark Office*